(12) United States Patent
O'Neill et al.

(10) Patent No.: US 7,935,489 B2
(45) Date of Patent: *May 3, 2011

(54) METHODS AND DEVICES FOR ANALYTE DETECTION

(75) Inventors: Roger A. O'Neill, San Carlos, CA (US);
Marc Glazer, Mountain View, CA (US);
Tom Weisan Yang, Cupertino, CA (US)

(73) Assignee: Cell Biosciences, Inc., Santa Clara, CA (US)

( * ) Notice: Subject to any disclaimer, the term of this patent is extended or adjusted under 35 U.S.C. 154(b) by 909 days.

This patent is subject to a terminal disclaimer.

(21) Appl. No.: 11/185,247

(22) Filed: Jul. 19, 2005

(65) Prior Publication Data

US 2006/0029978 A1 Feb. 9, 2006

Related U.S. Application Data

(60) Provisional application No. 60/589,139, filed on Jul. 19, 2004, provisional application No. 60/617,362, filed on Oct. 8, 2004.

(51) Int. Cl.
*G01N 33/50* (2006.01)
*G01N 33/53* (2006.01)
*G01N 33/536* (2006.01)
*G01N 33/543* (2006.01)
*G01N 21/00* (2006.01)
*G01N 21/63* (2006.01)
*G01N 21/64* (2006.01)

(52) U.S. Cl. ............ 435/7.1; 422/68.1; 422/81; 422/82; 422/82.05; 422/82.07; 422/82.09; 422/100; 422/101; 435/287.2; 435/288.5; 435/288.7; 435/164; 435/172

(58) Field of Classification Search .............. 422/82.05, 422/82.09, 101; 435/7.1; 436/164, 172
See application file for complete search history.

(56) References Cited

U.S. PATENT DOCUMENTS

| | | | |
|---|---|---|---|
| 4,666,855 A | 5/1987 | Yang et al. | |
| 4,680,201 A | 7/1987 | Hjerten | |
| 4,788,138 A | 11/1988 | Tung et al. | |
| 4,870,003 A | 9/1989 | Kortright et al. | |
| 4,921,790 A | 5/1990 | O'Brien | |
| 5,002,582 A | 3/1991 | Guire et al. | |
| 5,074,982 A | 12/1991 | Novotny et al. | |
| 5,137,609 A | 8/1992 | Manian et al. | |
| 5,290,418 A | 3/1994 | Menchen et al. | |
| 5,348,633 A | 9/1994 | Karger et al. | |
| 5,370,777 A | 12/1994 | Guttman et al. | |
| 5,376,249 A | 12/1994 | Afeyan et al. ........... 204/452 |
| 5,395,502 A | 3/1995 | Pawliszyn | |

(Continued)

FOREIGN PATENT DOCUMENTS

EP    0 665 430 A1    1/1994

(Continued)

OTHER PUBLICATIONS

Bossi et al., "Capillary electrophoresis coupled to biosensor detection," J. Chromatography A, 2000, vol. 892, pp. 143-153.*

(Continued)

*Primary Examiner* — Unsu Jung

(57) ABSTRACT

Methods for detecting one or more analytes, such as a protein, in a fluid path are provided. The methods include resolving, immobilizing and detecting one or more analytes in a fluid path, such as a capillary. Also included are devices and kits for performing such assays.

31 Claims, 15 Drawing Sheets

U.S. PATENT DOCUMENTS

| | | | |
|---|---|---|---|
| 5,468,365 A | | 11/1995 | Menchen et al. |
| 5,482,867 A | * | 1/1996 | Barrett et al. ............... 436/518 |
| 5,552,028 A | | 9/1996 | Madabhushi et al. |
| 5,567,292 A | | 10/1996 | Madabhushi et al. |
| 5,759,369 A | | 6/1998 | Menchen et al. |
| 5,759,770 A | | 6/1998 | Guertler et al. |
| 5,784,154 A | | 7/1998 | Pawliszyn |
| 5,785,926 A | | 7/1998 | Seubert et al. |
| 5,804,384 A | * | 9/1998 | Muller et al. ............... 435/6 |
| 5,830,539 A | | 11/1998 | Yan et al. ............... 427/551 |
| 5,840,388 A | | 11/1998 | Karger et al. |
| 5,840,503 A | * | 11/1998 | Beausang et al. ............ 435/7.21 |
| 5,843,680 A | | 12/1998 | Manian et al. |
| 5,866,683 A | | 2/1999 | Shimura et al. |
| 5,935,401 A | | 8/1999 | Amigo |
| 5,976,896 A | * | 11/1999 | Kumar et al. ............... 436/527 |
| 6,054,032 A | | 4/2000 | Haddad et al. ............... 204/451 |
| 6,056,860 A | | 5/2000 | Amigo |
| 6,074,542 A | | 6/2000 | Dolnik et al. |
| 6,100,045 A | * | 8/2000 | Van Es ............... 435/7.1 |
| 6,139,797 A | | 10/2000 | Suzuki et al. |
| 6,197,173 B1 | | 3/2001 | Kirkpatrick ............... 204/478 |
| 6,254,634 B1 | | 7/2001 | Anderson et al. |
| 6,348,596 B1 | | 2/2002 | Lee et al. |
| 6,355,709 B1 | | 3/2002 | Madabhushi et al. |
| 6,358,385 B1 | | 3/2002 | Madabhushi et al. |
| 6,375,817 B1 | * | 4/2002 | Taylor et al. ............... 204/453 |
| 6,395,503 B1 | | 5/2002 | Suzuki et al. |
| 6,423,536 B1 | | 7/2002 | Jovanovich et al. |
| 6,430,512 B1 | | 8/2002 | Gallagher |
| 6,787,016 B2 | | 9/2004 | Tan et al. |
| 6,818,112 B2 | | 11/2004 | Schneider et al. |
| 7,309,593 B2 | | 12/2007 | Ofstead et al. |
| 2002/0071847 A1 | | 6/2002 | Sadziene et al. |
| 2002/0123134 A1 | | 9/2002 | Huang et al. |
| 2003/0032035 A1 | | 2/2003 | Chatelain et al. |
| 2003/0175820 A1 | | 9/2003 | Smith et al. ............... 435/7.2 |
| 2003/0175986 A1 | | 9/2003 | Patricelli ............... 436/172 |
| 2004/0021068 A1 | | 2/2004 | Staats ............... 250/288 |
| 2004/0181443 A1 | | 9/2004 | Horton et al. ............... 705/8 |
| 2004/0262160 A1 | | 12/2004 | Schneider et al. |
| 2005/0054083 A1 | | 3/2005 | Vuong et al. ............... 435/287.2 |
| 2005/0082170 A1 | | 4/2005 | Provost et al. |
| 2005/0115837 A1 | | 6/2005 | Burgi |
| 2006/0029978 A1 | | 2/2006 | O'Neill et al. |
| 2006/0030669 A1 | | 2/2006 | Taton et al. |

FOREIGN PATENT DOCUMENTS

| | | |
|---|---|---|
| EP | 0 805 215 A | 11/1997 |
| JP | 05 172815 A | 7/1993 |
| WO | WO 94/13829 | 6/1994 |
| WO | WO 01/55721 A2 | 8/2001 |

OTHER PUBLICATIONS

Misiakos et al., "A multi-band capillary immunosensor," Biosensors & Bioelectronics, 1998, vol. 13, pp. 825-830.*

Narang et al., "Multianalyte detection using a capillary-based flow immunosensor," Anal. Biochem., 1998, vol. 255, pp. 13-19.*

Vilkner, Torsten, et al., "Micro Total Analysis Systems. Recent Developments", *Analytical Chemistry*, vol. 76, No. 12, Jun. 15, 2004, pp. 3373-3385.

Albarghouthi, M., et al., "Poly-*N*-hydroxyethylacrylamide as a novel, adsorbed coating for protein separation by capillary electrophoresis," *Electrophoresis* 24:1166-1175 (2003).

Chang, W., et al., "Enhanced resolution achieved with electroosmotic flow control in capillary isoelectric focusing with dynamic coatings," *Am. Biotechnol. Lab.* (Apr. 2005).

Doherty, E., et at., "Critical factors for high-performance physically adsorbed (dynamic) polymeric wall coatings for capillary electrophoresis of DNA," *Electrophoresis* 23:2766-2776 (2002).

International Preliminary Report on Patentability International Application No. PCT/US2005/025653, dated Jan. 23, 2007.

International Search Report in International Application No. PCT/US2005/025653, dated Dec. 22, 2005.

Written Opinion of the International Searching Authority International Application No. PCT/US2005/025653, dated Dec. 22, 2005.

International Search Report and the Written Opinion of International Searching Authority, or the Declaration, for counterpart or related PCT Application Serial No. PCT/US 06/13447, dated Aug. 17, 2007.

International Search Report and the Written Opinion of International Searching Authority, or the Declaration, for counterpart or related PCT Application Serial No. PCT/US 06/36808, dated Sep. 18, 2007.

Hu, Shen, et al., "Capillary sodium dodecyl sulfate-DALT electrophoresis of proteins in a single human cancer cell," *Electrophoresis* 22:3677-3682 (2001).

Shimura, et al, "Synthectic oligopeptides as isoelectric point markers for capillary isoelectric focusing with ultraviolet absorption detection" *Electrophoresis*; 21, pp. 603-610 (2002).

Ya, Jin, et al. Estimation of isoelectric points of human plasma proteins employing capillary isoelectric focusing and peptide isoelectric point marks, *Electrophoresis* 23:3385-3391 (2002).

Wang, J., et al. "Capillary Electrophoresis Immunoassay Chemiluminescence Detection of Zeptomoles of Bone Morphogenic Protein-2 in Rat Vascular Smooth Muscle Cells", Anal Chem 76, 5393-5398 (2004).

Watts, R. M., et al. "Peptides as standards for denaturing isoelectric focusing" *Electrophoresis* 16:22-27 (1995).

International Search Report for PCT Application No. PCT/US2007/016626 dated Apr. 28, 2008, 2 pages.

Annex to form PCT/ISA/206 Communication Relating to the Results of the Partial International Search for PCT/US2008/081637.

Bossi, et al., "Capillary Electrophoresis Coupled to Biosensor Detection," J. Chromatography A, 2000, vol. 892, pp. 143-153.

Burnette, W. N., "Western Blotting": Electrophoretic Transfer of Proteins from Sodium Dodecyl Sulfate-Polyacrylamide Gels to Unmodified Nitrocellulose and Radiographic Detection with Antibody and Radioiodinated Protein A, Analytical Biochemistry 112, 1981, pp. 195-203.

Cruickshank, K., et al. "Simultaneous Multiple Analyte Detection Using Fluorescent Peptides and Capillary Isoelectric Focusing," Journal of Chromatography A, 817, 1998, pp. 41-47.

Office Action for U.S. Appl. No. 11/431,272 dated Mar. 20, 2009.

Renart, J. et al., "Transfer of Proteins from Gels to Diazobenzyloxymethyl-paper and Detection with Antisera: A Method for Studying Antibody Specificity and Antigen Structure," Jul. 1979, Proc. Natl. Acad., Sci., USA, vol. 76, No. 7, pp. 3116-3120.

Righetti, P., et al., "Capillary Isolelectric Focusing and Isoelectric Buffers: An Evolving Scenario," J Cap Elec. 004, vol. 4, Issue 2, Mar./Apr. 1997, pp. 47-59.

Shimura, K., et al., "Fluorescence-Labeled Peptide p/ Markers for Capillary Isoelectric Focusing," Anal. Chem. 2002, vol. 74, pp. 1046-1053.

Wehr, T., "Capillary Isoelectric Focusing," Methods in Enzymology, vol. 270, pp. 358-374.

International Search Report and Written Opinion for PCT/US2008/081637 dated Jul. 9, 2009.

* cited by examiner

METHODS AND DEVICES FOR ANALYTE DETECTION

1. CROSS REFERENCES TO RELATED APPLICATIONS

This application claims benefit under 35 U.S.C. §119(e) to application Ser. No. 60/589,139, entitled "Continuous Determination of Cellular Contents by Chemiluminescence," filed Jul. 19, 2004 and application Ser. No. 60/617,362, entitled "Determination of Captured Cellular Contents," filed Oct. 8, 2004, the disclosures of which are incorporated herein by reference in their entireties.

2. FIELD OF INVENTION

The present invention relates to methods, devices and kits for analyte detection and various uses thereof.

3. INTRODUCTION

Methods and devices for detecting analytes are important tools for characterizing analytes in biological and industrial applications. In many applications, it is desirable to detect the presence of one or more analytes in a sample. For example, rapid detection of a particular protein in a mixture of proteins is particularly useful in molecular biology protocols, drug development and disease diagnosis.

Although numerous approaches have been developed for detecting analytes, there is still a great need to find new assay designs that can be used to inexpensively and conveniently detect and characterize a wide variety of analytes. However, currently available assay protocols are inconvenient, expensive, or have other deficiencies. For example, Western blotting has been in widespread use for more than two decades for detecting proteins. In this technique, a sheet of gel is retained between two plates and usually is mounted vertically with the upper edge of the gel sheet accessible to the sample to be assayed. The sample is applied in wells created along the upper edge of the gel and an electrophoretic potential is applied between the upper and lower edges of the sheet of gel. The electrophoretic potential is applied by a DC power supply, and may be in the range of 50 to more than 1000 volts. The electrophoretic potential is applied for a period of time that allows the proteins in the sample, to distribute themselves (i.e., separate) vertically through the sheet of gel, typically for 1-4 hours, but in some cases considerably longer. The potential must be removed when the proteins are distributed as desired. The sheet of gel is then removed from between its two glass retaining plates and is then placed on a sheet of blotting material such as porous nitrocellulose of length and width dimensions approximately matching those of the sheet of gel, the blotting material having already been soaked in a buffer to hydrate it. Care must be taken at this step to avoid the presence of air bubbles between the gel and the blotting material, which would impede the direct transfer of the distributed proteins from the gel to the blotting material. Two electrode plates are then placed on either side of the gel and blotting material, thereby sandwiching the sheets of gel and blotting material between the electrode plates. The electrode plates should preferably apply a uniform electrophoretic field across the thicknesses of the sheets of gel and blotting material. This electrophoretic field, typically 100-500 volts, transfers the proteins from the gel to the blotting material in the same distribution in which they were captured in the gel matrix. This transfer process takes approximately 1-2 hours, but can take as much as overnight for some proteins to be transferred.

After the proteins adhere to the blotting material, the blotting material is removed from the sandwich and is washed in a buffer containing one or more blocking agents such as skim milk, bovine serum albumin or tween-20 detergent for 1-4 hours and then is immersed in a solution of protein-specific reporter antibodies. During the immersion the blotting paper is typically agitated by a rocking or circular motion in the plane of the blotting paper. The immersion step typically takes 1-4 hours, but can take overnight or longer for some antibody-protein pairs. Reporter antibody detection can be done with a variety of markers such as optical dyes, radioactive or chromogenic markers, fluorescent dyes or reporter enzymes depending upon the analytical method used. These results are known as Western blots as described by Towbin H., Staehelin T., and Gordon J., Proc. Nat. Acad. Sci. USA, 76: 4350-4354 (1979), Bumette W. N., Anal. Biochem., 112: 195-203 (1981), and Rybicki & von Wechmar in J. Virol. Methods, vol. 5: 267-278 (1982).

The Western blot technique, while widely used, has a number of drawbacks and deficiencies. First, as the above description makes clear, the processing is very complex. There are many distinctly different steps, including the step of initially distributing the proteins being analyzed through the gel, the intermediate step of transferring the distributed proteins to the blotting material, the later step of binding the reporter antibodies, and the final step of reading or analyzing the results. Between these major steps are preparation steps and washing the variously processed components of the technique. Second, there is extensive handling of the components of the technique. The gel must be placed in the distribution apparatus, then removed and located in the blotting apparatus, then the blotting material must be handled to bind the reporter substrates. The components can be damaged during this handling, in particular the fragile sheet of gel. Third, it takes a considerable amount of time to arrive at just a single blot. At least a day is required to produce just one blot, and generally 1½-2 days are required. During the beginning of the process the accuracy of the technique is affected by migration of the proteins until they are immobilized in the blotting material, which can result in band broadening. Fourth, the variability introduced by the complexity of the handling and processing can require the process to be repeated several times before acceptable results are obtained. Fifth, the variability in the results often requires subjective decisions to be made in reading the results of the blot. This subjectivity reduces the ability to obtain quantifiable, objective results and frequently limits the technique to practice by highly trained and experienced personnel. Sixth, the variability and complexity of the process impedes the ability to automate the process. Seventh, the technique has low sensitivity and generally is only effective with the contents of hundreds of thousands or millions of cells. Certainly, the technique cannot be used to analyze the enzymes of an individual mammalian cell. Eighth, the quantitation of the technique is poor. For one example, the agitation process may fail to cause the uniform binding of reporter substrates to the analytes in the blotting material. For another example, in the electroblotting step the time required to transfer some proteins is sufficient to enable other proteins to pass through the blotting membrane and be lost. Finally, the process can require large quantities of expensive probe and reporter antibodies to be used. In sum, the Western gel blotting technique is generally complex, time-consuming, expensive, insensitive and inexact.

Thus, although numerous approaches have been developed for detecting analytes, there is still a great need to find new methods and devices that can be used to conveniently and sensitively detect and characterize a wide variety of analytes.

4. SUMMARY

The present invention provides methods, devices, and kits for detecting one or more analytes of interest in a sample. In some embodiments, methods of detecting at least one analyte in a sample are provided, characterized in that: one or more analytes are resolved in a fluid path and the analyte(s) are immobilized in the fluid path. Detection agents are conveyed through the fluid path which bind to or interact with the analyte(s) and permit detection of the immobilized analyte(s) in the fluid path.

In another aspect, methods for detecting at least one protein in a sample are provided comprising the steps of: resolving one or more proteins in a capillary, photoimmobilizing one or more proteins in the capillary, contacting antibodies with the immobilized protein(s) to form antibody-protein complex(es) in the capillary, and detecting the protein(s).

In a further aspect, methods of detecting at least one protein in a sample are provided wherein one or more target proteins are resolved in a capillary. The capillary comprises at least one or more photoreactive groups. In some embodiments, the capillary comprises polymeric material or polymerizable material comprising one or more photoreactive groups. The protein(s) are photoimmobilized in the capillary. Antibodies are then contacted with the photoimmobilized proteins and form antibody-protein complex(es) in the capillary, and the proteins are detected.

Further methods of detecting at least one protein in a sample are provided comprising the steps of: concentrating one or more proteins in a fluid path, immobilizing the protein(s) in the fluid path; contacting the immobilized target protein(s) with detection agents to form a detection agent-protein complex(es) in the fluid path, and detecting the target protein.

Additionally, systems for detecting at least one analyte in a sample are provided, comprising a fluid path with one or more reactive groups contained therein, where the reactive groups are capable of immobilizing the analyte(s) in the fluid path. A power supply is coupled to the fluid path and is configured to apply a voltage along the fluid path wherein the analytes are resolved in the fluid path. A detector is provided which detects the analytes immobilized in the fluid path.

In another aspect, kits for detecting at least one analyte in a sample are provided, comprising one or more fluid paths comprising one or more reactive moieties, buffer and detection agents.

These and other features of the present teachings are set forth below.

5. BRIEF DESCRIPTION OF THE DRAWINGS

The skilled artisan will understand that the drawings, described below, are for illustration purposes only. The drawings are not intended to limit the scope of the present teachings in any way.

FIGS. 1a-d illustrate exemplary embodiments of resolving, immobilizing and labeling cellular materials in a capillary.

FIGS. 2a-b illustrate exemplary embodiments of immobilizing resolved analytes in a polymeric material in a capillary.

FIGS. 3a-h illustrate exemplary embodiments of detecting one or more analytes.

Figure 12A:
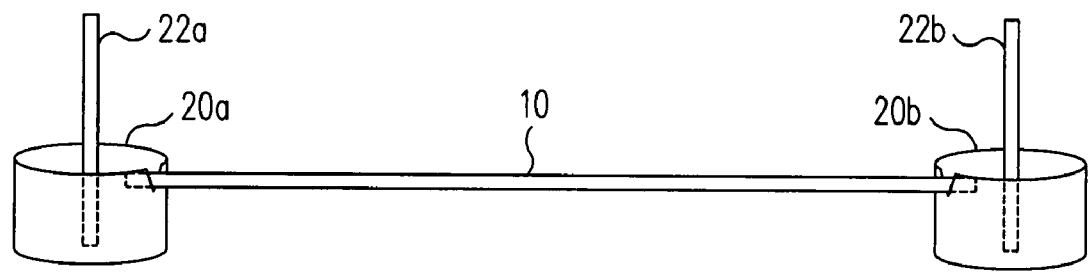
Figure 12B:
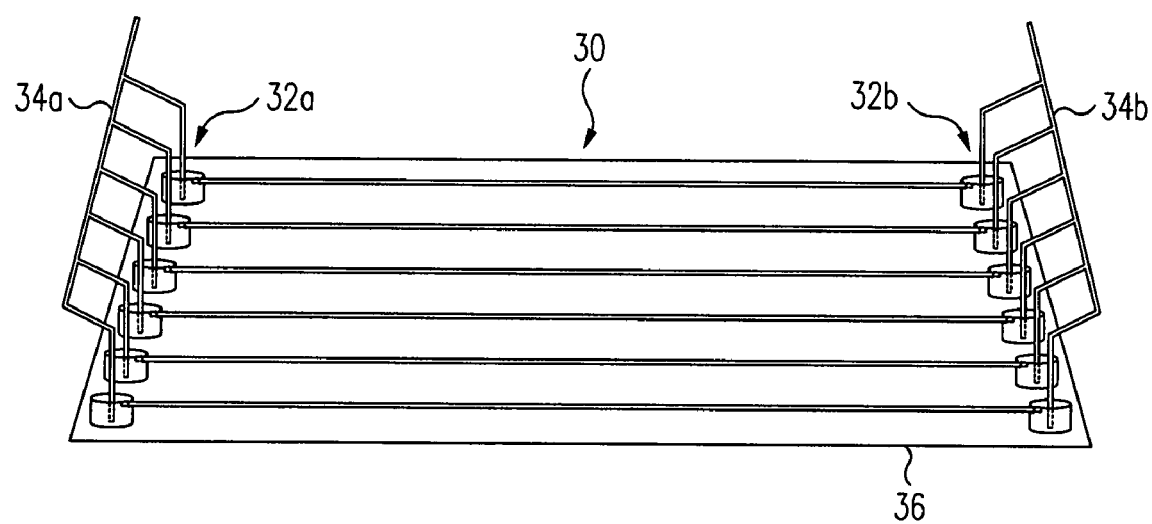

FIGS. 12a-b illustrate exemplary embodiments of (a) a capillary between two fluid-filled wells and electrodes and (b) a capillary array device.

Figure 13:
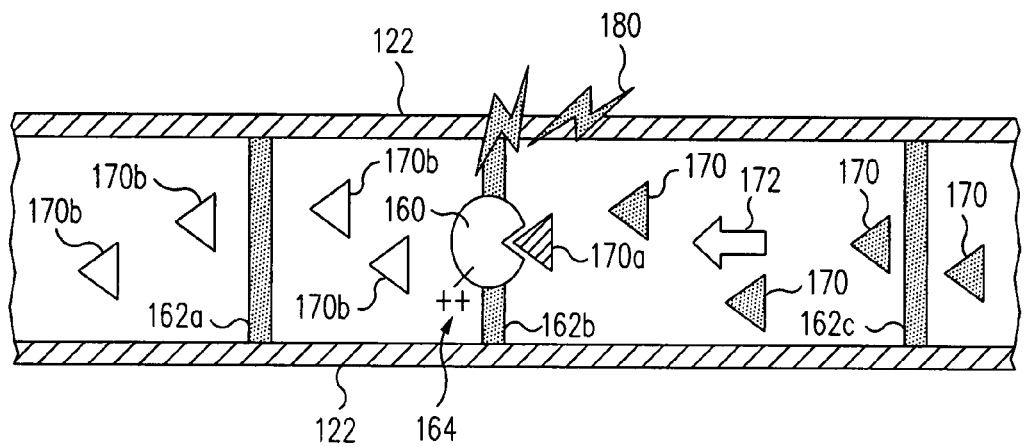

FIG. 13 illustrates an exemplary embodiment of an analytical system detection of cellular materials in a capillary by chemiluminescence.

Figure 14:
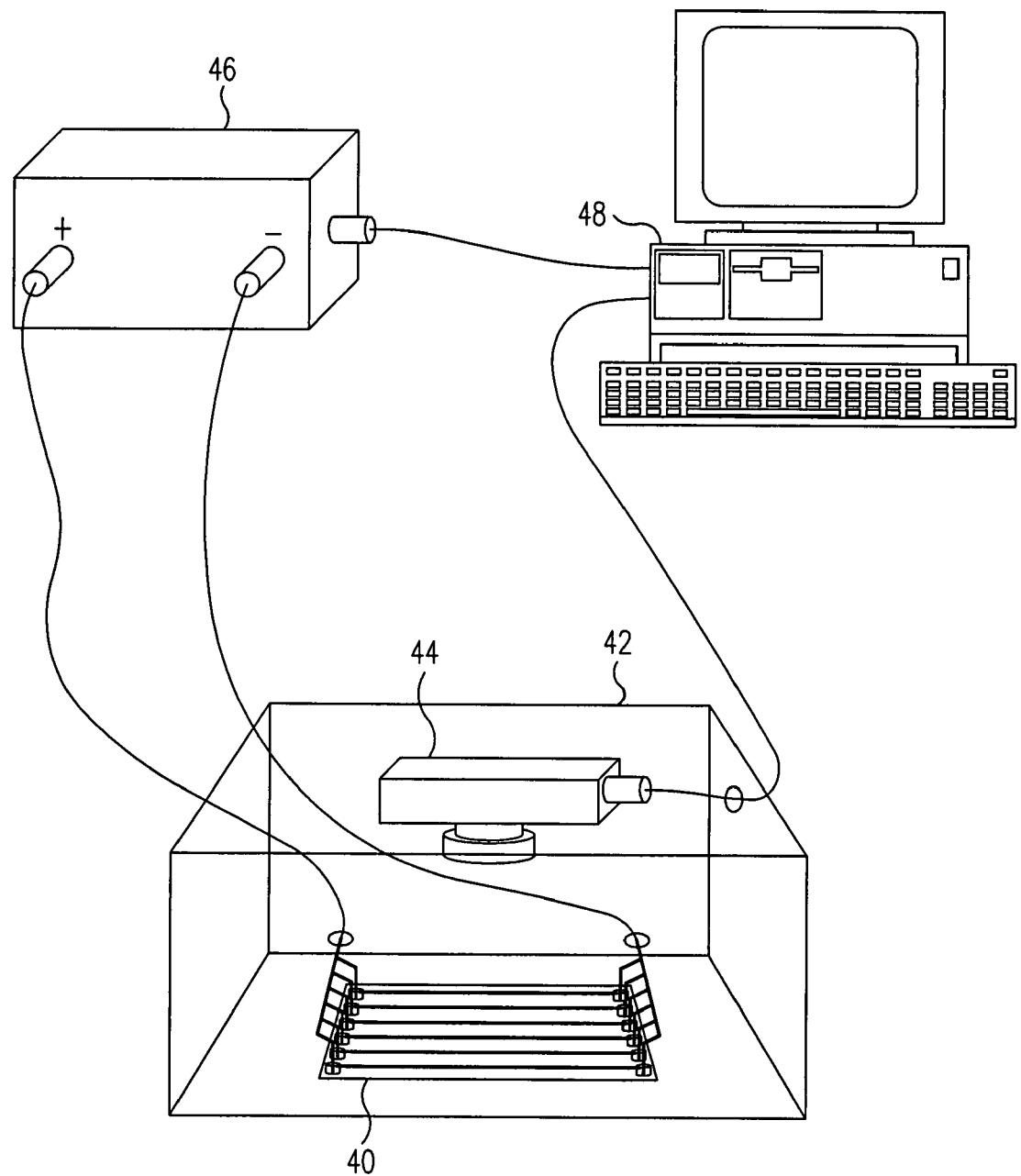

FIG. 14 illustrates an exemplary embodiment of an analytical device.

Figure 15:
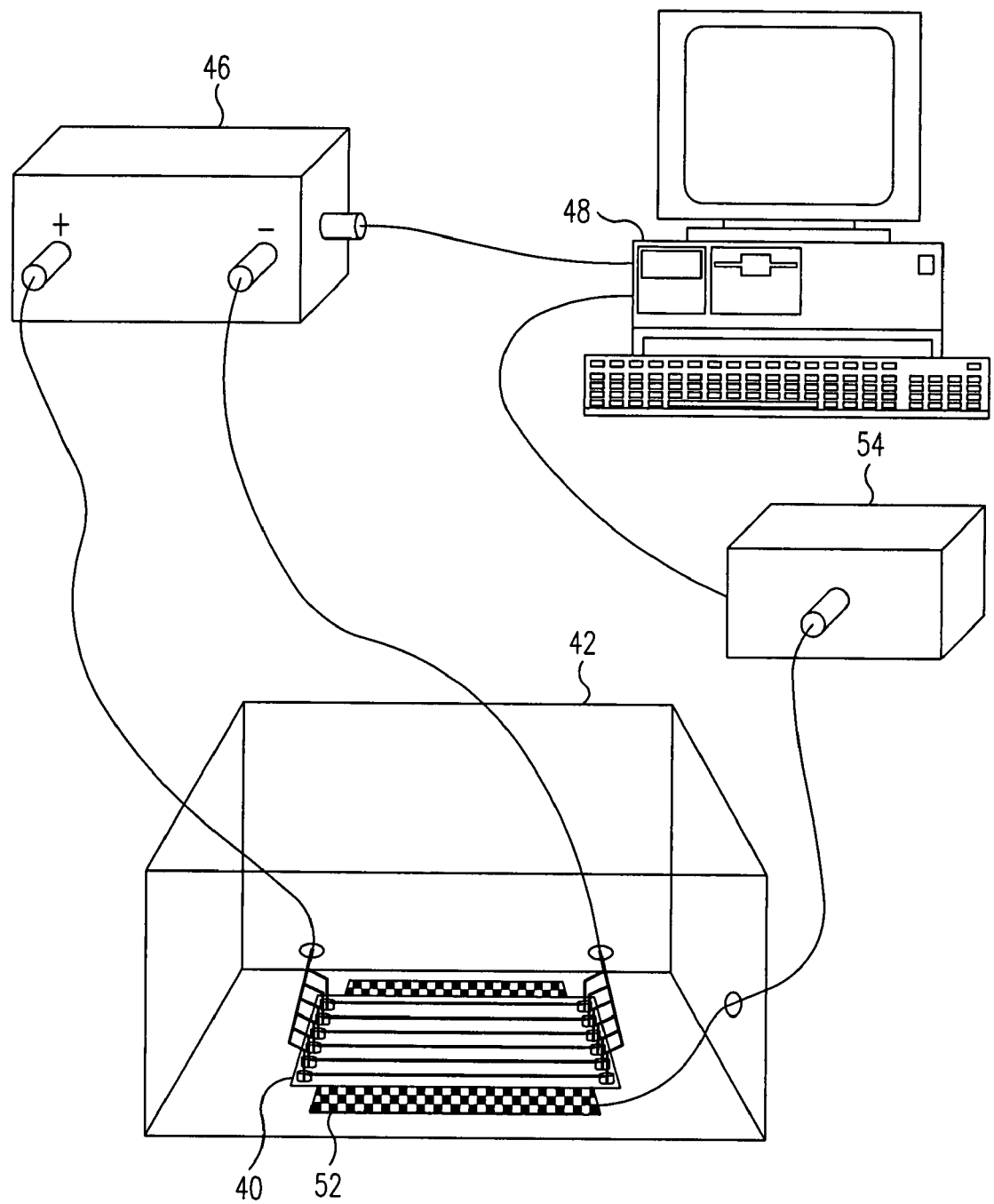

FIG. 15 illustrates an exemplary embodiment of an analytical device.

Figure 16:
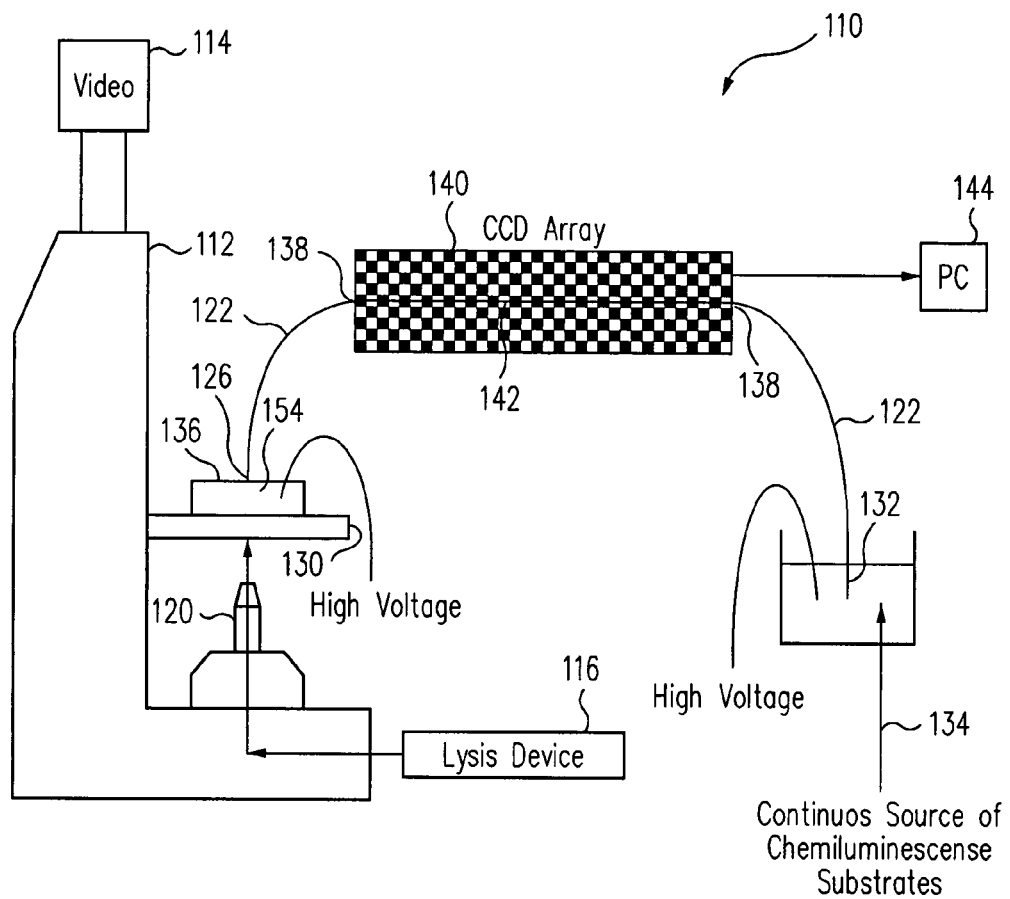

FIG. 16 illustrates an exemplary embodiment of an analytical device.

Figure 17:
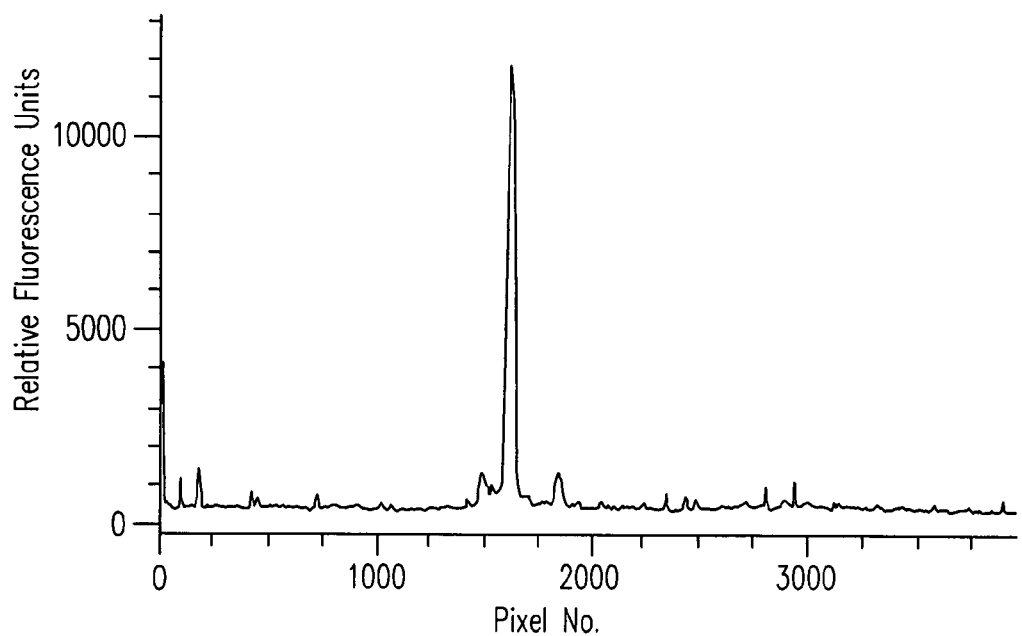

FIG. 17 illustrates fluorescent detection of Green Fluorescent Protein.

Figure 18:
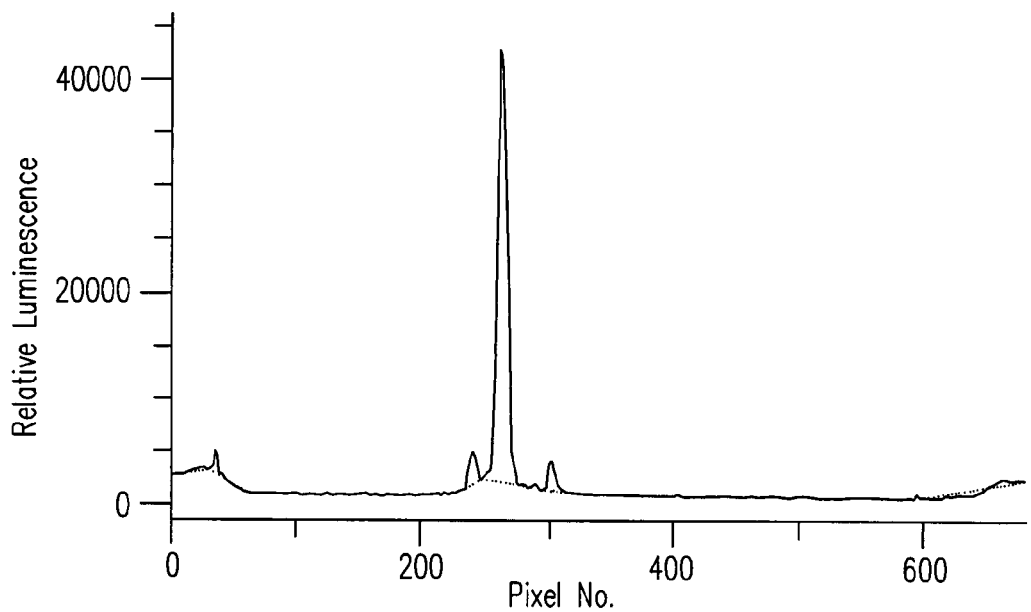

FIG. 18 illustrates chemiluminescent detection of Green Fluorescent Protein.

Figure 19:
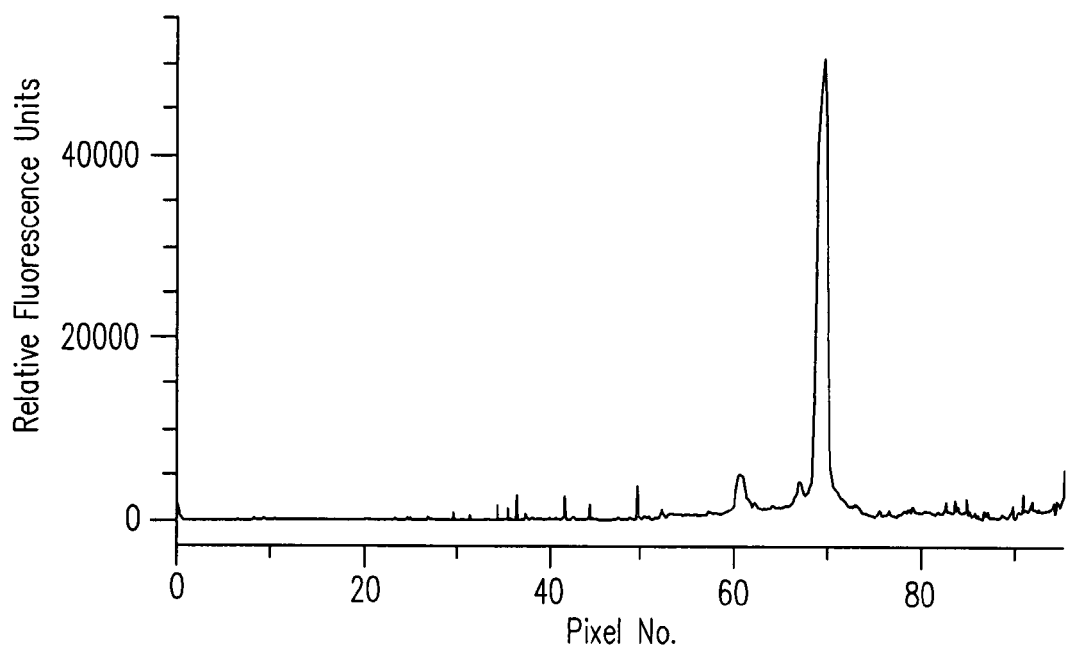

FIG. 19 illustrates fluorescent detection of horse myoglobin.

Figure 20:
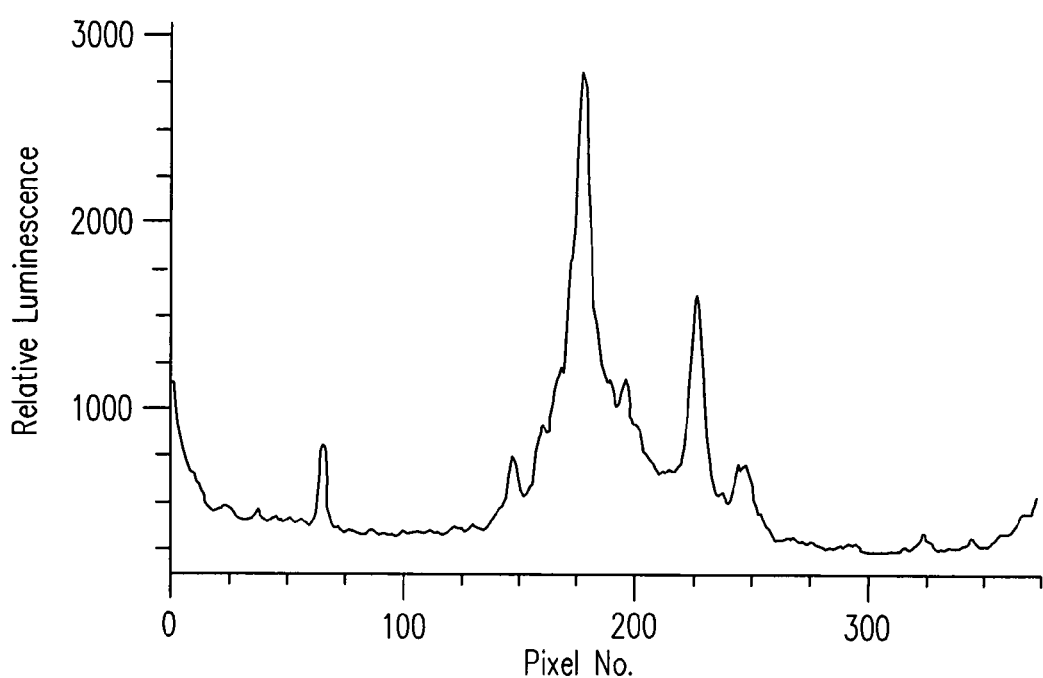

FIG. 20 illustrates chemiluminescent detection of Akt protein.

Figure 21:
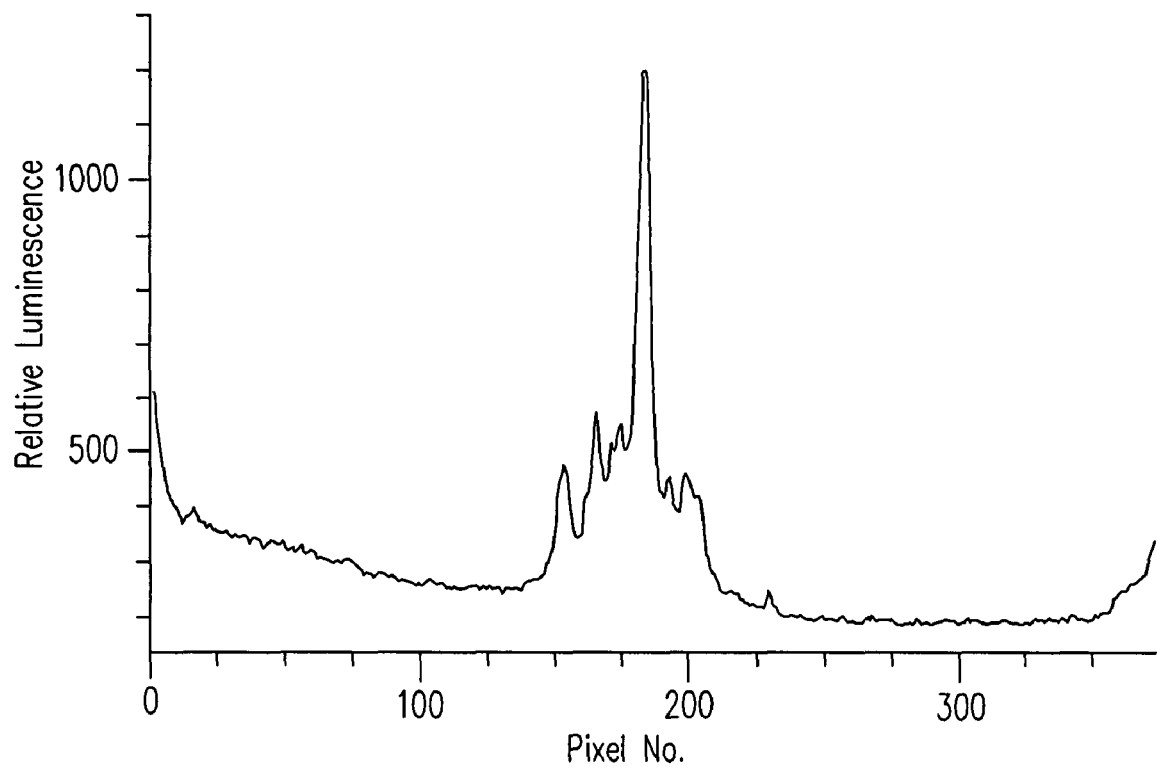

FIG. 21 illustrates chemiluminescent detection of phosphorylated Akt protein.

Figure 22:
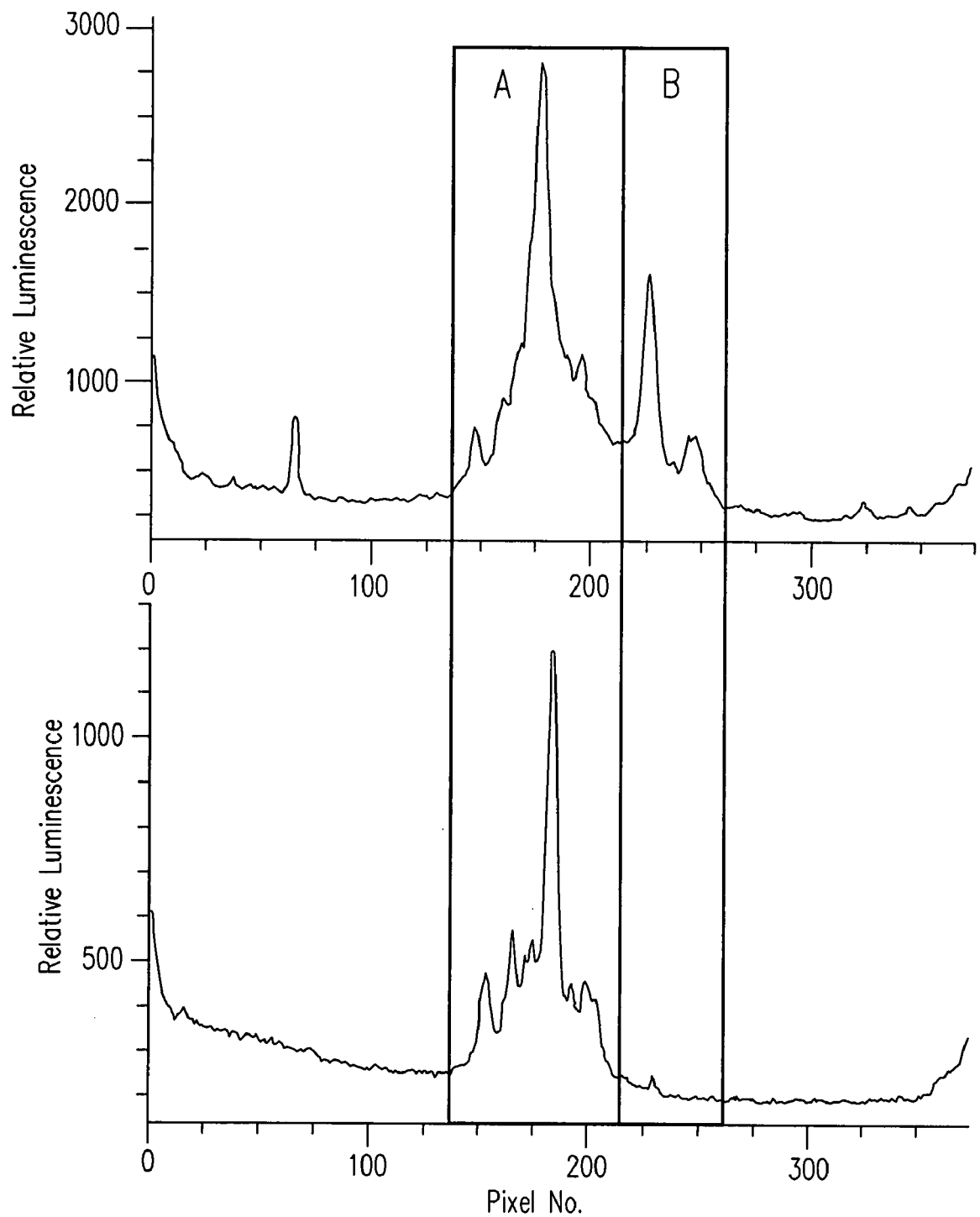

FIG. 22 illustrates chemiluminescence detection of Akt protein and phosphorylated Akt protein.

6. DETAILED DESCRIPTION OF EMBODIMENTS

It is to be understood that both the foregoing general description and the following description are exemplary and explanatory only and are not restrictive of the methods and devices described herein. In this application, the use of the singular includes the plural unless specifically state otherwise. Also, the use of "or" means "and/or" unless state otherwise. Similarly, "comprise," "comprises," "comprising," "include," "includes" and "including" are not intended to be limiting.

6.1 Definitions

As used throughout the instant application, the following terms shall have the following meanings:

"Antibody" has its standard meaning and is intended to refer to full-length as well antibody fragments, as are known in the art, including Fab, $Fab_2$, single chain antibodies (Fv for example), monoclonal, polyclonal, chimeric antibodies, etc., either produced by the modification of whole antibodies or those synthesized de novo using recombinant DNA technologies.

"Detect" and "detection" have their standard meaning, and are intended to encompass detection including the presence or absence, measurement, and/or characterization of an analyte.

"Label" as used herein refers to a detectable moiety. As will be appreciated by those in the art, suitable labels encompass a wide variety of possible moieties. In general, labels include, but are not limited to, a) isotopic labels, which may be radioactive or heavy isotopes; b) immune labels, which may be antibodies or antigens; c) optical dyes, including colored or fluorescent dyes; d) enzymes such as alkaline phosphatase and horseradish peroxidase, e) particles such as colloids, magnetic particles, etc., and combinations thereof such as fluorescent labeled antibodies, and chemiluminescent labeled antibodies.

"Protein" has its standard meaning and is intended to refer to proteins, oligopeptides and peptides, derivatives and analogs, including proteins containing non-naturally occurring amino acids and amino acid analogs, and peptidomimetic structures, and includes proteins made using recombinant techniques, i.e. through the expression of a recombinant nucleic acid.

6.2 Methods

Provided herein are methods of detecting one or more analytes in a sample. In some embodiments, methods of detecting at least one analyte in a sample are provided, characterized in that: one or more analytes are resolved in a fluid path and the analyte(s) are immobilized in the fluid path. Detection agents are conveyed through the fluid path, which bind to or interact with the analytes and permit detection of the immobilized analytes in the fluid path.

In some embodiments, methods of detecting at least one analyte of interest in a sample are provided. In some embodiments, the method comprises resolving one or more analytes in a fluid path, immobilizing the analytes in the fluid path, and contacting the immobilized analytes with detection agents, and detecting the analytes. In some embodiments, the method comprises separating a sample into two or more components in a fluid path, immobilizing one or more analytes of interest in the fluid path, and contacting the immobilized analytes with detection agents, and detecting the analytes.

The sample contains the analyte or analytes to be detected. The sample can be heterogeneous, containing a variety of components, i.e. different proteins. Alternatively, the sample can be homogenous, containing one component. The sample can be naturally occurring, a biological material, or man-made material. For example, the sample can be a single cell or a plurality of cells, a blood sample, a tissue sample, a skin sample, a urine sample, a water sample, or a soil sample. In some embodiments, the sample comprises the contents of a single cell, or the contents of a plurality of cells. The sample can be from a living organism, such as a eukaryote, prokaryote, mammal, human, yeast, or bacterium, or the sample can be from a virus. In some embodiments, sequential samples can be assayed from a single animal, such as sequential cuttings from a rodent tail over time.

In some embodiments, the sample can be one or more stem cells. A stem cell is any cell that has the ability to divide for indefinite periods of time and to give rise to specialized cells. Suitable examples include embryonic stem cells, such as human embryonic stem cells (hES), and non-embryonic stems cells, such as mesenchymal, hematopoietic, or adult stem cells (MSC).

As will be appreciated by those skilled in the art, virtually any processing may be performed on the sample prior to detecting the analyte. For example, the sample can be subjected to a lysing step, denaturation step, heating step, purification step, precipitation step, immunoprecipitation step, column chromatography step, centrifugation, etc. In some embodiments, the separation of the sample and immobilization may be performed on native substrates, the analyte of interest, i.e. a protein, or may also undergo denaturation to expose their internal hydrophobic groups for immobilizing in the fluid path.

The analyte to be detected can be any analyte selected by the user. The analyte can comprise any organic or inorganic molecule capable of being detected. Non-limiting examples of analytes that can be detected include proteins, oligopeptides and peptides, derivatives and analogs, including proteins containing non-naturally occurring amino acids and amino acid analogs. Other example of analytes that can be detected include carbohydrates, polysaccharides, glycoproteins, viruses, metabolites, cofactors, nucleotides, polynucleotides, transition state analogs, inhibitors, drugs, nutrients, electrolytes, hormones, growth factors and other biomolecules as well as non-biomolecules, as well as fragments and combinations of all the forgoing.

As will be appreciated by those in the art, virtually any method of loading the sample in the fluid path may be performed. For example, the sample can be loaded into one end of the fluid path. In some embodiments, the sample is loaded into one end of the fluid path by hydrodynamic flow. For example, in embodiments wherein the fluid path is a capillary, the sample can be loaded into one end of the capillary by hydrodynamic flow, such that the capillary is used as a micropipette. FIG. 3b illustrates an exemplary embodiment of loading a sample in capillary by capillary action. In some embodiments, the sample can be loaded into the fluid path by electrophoresis, for example, when the fluid path is gel filled and therefore more resistant to hydrodynamic flow.

The fluid path can comprise any structure that allows liquid or dissolved molecules to flow. Thus, the fluid path can comprise any structure known in the art, so long as it is compatible with the methods and devices described herein. In some embodiments, the fluid path is a bore or channel through which a liquid or dissolved molecule can flow. In some embodiments, the fluid path is passage in a permeable material in which liquids or dissolved molecules can flow.

The fluid path comprises any material that allows the detection of the analyte within the fluid path. The fluid path comprises any convenient material, such as glass, plastic, silicon, fused silica, gel, or the like. In some embodiments, the method employs a plurality of fluid paths. A plurality of fluid paths enables multiple samples to be analyzed simultaneously.

The fluid path can vary as to dimensions, width, depth and cross-section, as well as shape, being rounded, trapezoidal, rectangular, etc., for example. The fluid path can be straight, rounded, serpentine, or the like. As described below, the length of the fluid path depends in part on factors such as sample size and the extent of sample separation required to resolve the analyte or analytes of interest.

In some embodiments, the fluid path comprises a tube with a bore, such as a capillary. In some embodiments, the method employs a plurality of capillaries. Suitable sizes include, but are not limited to, capillaries having internal diameters of about 10 to about 1000 μm, although more typically capillaries having internal diameters of about 25 to about 400 μm can be utilized. Smaller diameter capillaries use relatively low sample loads while the use of relatively large bore capillaries allows relatively high sample loads and can result in improved signal detection.

The capillaries can have varying lengths. Suitable lengths include, but are not limited to, capillaries of about 2 to 20 cm in length, although somewhat shorter and longer capillaries can be used. In some embodiments, the capillary is about 3, 4, 5, or 6 cms in length. Longer capillaries typically result in better separations and improved resolution of complex mixtures. Longer capillaries can be of particular use in resolving low abundance analytes.

Generally, the capillaries are composed of fused silica, although plastic capillaries and PYREX (i.e., amorphous glass) can be utilized. As noted above, the capillaries do not need to have a round or tubular shape, other shapes, so long as it is compatible with the methods and devices described herein can also be utilized.

In some embodiments, the fluid path can be a channel. In some embodiments, the method employs a plurality of channels. In some embodiments, the fluid path can be a channel in a microfluidic device. Microfluidics employs channels in a substrate to perform a wide variety of operations. The microfluidic devices can comprise one or a plurality of channels contoured into a surface of a substrate. The microfluidic device can be obtained from a solid inert substrate, and in some embodiments in the form of a chip. The dimensions of the microfluidic device are not critical, but in some embodiments the dimensions are in the order of about 100 μm to about 5 mm thick and approximately about 1 centimeters to about 20 centimeters on a side. Suitable sizes include, but are not limited to, channels having a depth of about 5 μm to about 200 μm, although more typically having a depth of about 20 μm to about 100 μm can be utilized. Smaller channels, such as micro or nanochannels can also be used, so long as it is compatible with the methods and devices described herein.

In some embodiments, the fluid path comprises a gel. In some embodiments, the gel is capable of separating the components of the sample based on molecular weight. A wide variety of such gels are known in the art, a non-limiting example includes a polyacrylamide gel.

The methods generally comprise resolving one or more analytes, contained in a sample, in the fluid path. Methods of separating a mixture into two or more components are well know to those of ordinary skill in the art, and may include, but are not limited to, various kinds of electrophoresis. As used herein, electrophoresis refers to the movement of suspended or dissolved molecules through a fluid or gel under the action of an electromotive force applied to electrodes in contact with a fluid.

In some embodiments, resolving one or more analytes comprises isoelectric focusing (IEF) of a sample. In an electric field, a molecule will migrate towards the pole (cathode or anode) that carries a charge opposite to the net charge carried by the molecule. This net charge depends in part on the pH of the medium in which the molecule is migrating. One common electrophoretic procedure is to establish solutions having different pH values at each end of an electric field, with a gradient range of pH in between. At a certain pH, the isoelectric point of a molecule is obtained and the molecule carries no net charge. As the molecule crosses the pH gradient, it reaches a spot where its net charge is zero (i.e., its isoelectric point) and it is thereafter immobile in the electric field. Thus, this electrophoresis procedure separates molecules according to their different isoelectric points.

In some embodiments, for example when resolving is by isoelectric focusing, an ampholyte reagent can be loaded into the fluid path. An ampholyte reagent is a mixture of molecules having a range of different isoelectric points. Typical ampholyte reagents are Pharmalyte™ and Ampholine™ available from Amersham Biosciences of Buckinghamshire, England. Ampholytes can be supplied at either end of the fluid path, or both, by pumping, capillary action, gravity flow, electroendosmotic pumping, or electrophoresis, or by gravity siphon that can extend continuously through the fluid path.

In some embodiments, resolving one or more analytes comprises electrophoresis of a sample in a polymeric gel. Electrophoresis in a polymeric gel, such as a polyacrylamide gel or an agarose gel separates molecules on the basis of the molecule's size. A polymeric gel provides a porous passageway through which the molecules can travel. Polymeric gels permit the separation of molecules by molecular size because larger molecules will travel more slowly through the gel than smaller molecules.

In some embodiments, resolving one or more analytes comprises micellar electrokinetic chromatography (MEKC) of a sample. In micellar electrokinetic chromatography, ionic surfactants are added to the sample to form micelles. Micelles have a structure in which the hydrophobic moieties of the surfactant are in the interior and the charged moieties are on the exterior. The separation of analyte molecules is based on the interaction of these solutes with the micelles. The stronger the interaction, the longer the solutes migrate with the micelle. The selectivity of MEKC can be controlled by the choice of surfactant and also by the addition of modifiers to the sample. Micellar electrokinetic chromatography allows the separation of neutral molecules as well as charged molecules.

The methods comprise immobilizing one or more resolved analytes in the fluid path. As used herein, immobilizing refers to substantially reducing or eliminating the motion of molecules in the fluid path. The immobilization can be via covalent bonds or non-covalent means such as by hydrophobic or ionic interaction. In some embodiments, the resolved analytes of the sample are immobilized in the fluid path by isoelectric focusing.

In some embodiments, the fluid path comprises one or more reactive moieties. A reactive moiety can be used to covalently immobilize the resolved analyte or analytes in the fluid path. The reactive moiety can comprise any reactive group that is capable of forming a covalent linkage with a corresponding reactive group of individual molecules of the sample. Thus, the reactive moiety can comprise any reactive group known in the art, so long as it is compatible with the methods and devices described herein. In some embodiments, the reactive moiety comprises a reactive group that is capable of forming a covalent linkage with a corresponding reactive group of an analyte of interest. In embodiments employing two or more reactive moieties, each reactive moiety can be the same, or some or all of the reactive moieties may differ.

The reactive moiety can be attached directly, or indirectly to the fluid path. In some embodiments, the reactive moiety can be supplied in solution or suspension, and may form bridges between the wall of the fluid path and the molecules in the sample upon activation. The reactive moiety can line the fluid path or, in another embodiment, may be present on a linear or cross-linked polymer in the fluid path. The polymer may or may not be linked to the wall of the fluid path before and/or after activation.

A wide variety of reactive moieties suitable for covalently linking two molecules together are well-known. The actual choice of reactive moieties will depend upon a variety of factors, and will be apparent to those of skill in the art. For example, the reactive moiety can bind to carbon-hydrogen (C—H) bonds of proteins. Since many separation media also contain components with C—H bonds, chemistries that react with sulfhydryl (S—H) groups may be advantageous in that S—H groups are found uniquely on proteins relative to most separation media components. Chemistries that react with amine or carboxyl groups may also be advantageous due to the prevalence of such groups on proteins.

Suitable reactive moieties include, but are not limited to, photoreactive groups, chemical reactive groups, and thermoreactive groups.

Photoimmobilization in the fluid path can be accomplished by the activation of one or more photoreactive groups. A photoreactive group comprises one or more latent photoreactive groups that upon activation by an external energy source, forms a covalent bond with other molecules. See, e.g., U.S. Pat. Nos. 5,002,582 and 6,254,634, the disclosures of which are incorporated herein by reference. The photoreactive groups generate active species such as free radicals and particularly nitrenes, carbenes, and excited states of ketones upon absorption of electromagnetic energy. The photoreactive groups can be chosen that are responsive to various portions of the electromagnetic spectrum, such as those responsive to ultraviolet, infrared and visible portions of the spectrum. For example, upon exposure to a light source, the photoreactive group can be activated to form a covalent bond with an adjacent molecule.

Suitable photoreactive groups include, but are not limited to, aryl ketones, azides, diazos, diazirines, and quinones.

In some embodiments, the photoreactive group comprises aryl ketones, such as benzophenone, acetophenone, anthraquinone, anthrone, and anthrone-like heterocycles or their substituted derivatives. Benzophenone is a preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom to create a radical pair. The subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source.

In some embodiments, the photoreactive group comprises azides, such as arylazides such as phenyl azide, 4-fluoro-3-nitrophenyl azide, acyl azides such as benzoyl azide and p-methylbenzoyl azide, azido formates such as ethyl azidoformate, phenyl azidoformate, sulfonyl azides such as benzenesulfonyl azide, and phosphoryl azides such as diphenyl phosphoryl azide and diethyl phosphoryl azide.

In some embodiments, the photoreactive group comprises diazo compounds and includes diazoalkanes such as diazomethane and diphenyldiazomethane, diazoketones such as diazoacetophenone and 1-trifluoromethyl-1-diazo-2-pentanone, diazoacetates such as t-butyl diazoacetate and phenyl diazoacetate, and beta-keto-alpha-diazoacetates such as t-butyl alpha diazoacetoacetate.

In some embodiments, the photoreactive group comprises diazirines such as 3-trifluoromethyl-3-phenyldiazirine, and photoreactive group comprises ketenes such diphenylketene.

In some emdodiments, the photoreactive group comprises a N-((2-pyridyldithio)ethyl)-4-azidosalicylamide, 4-azido-2,3,5,6-tetrafluorobenzoic acid, 4-azido-2,3,5,6-tetrafluorobenzyl amine, benzophenone-4-maleimide, benzophenone-4-isothiocyanate, or 4-benzoylbenzoic acid.

As described above, in embodiments employing two or more reactive moieties, each reactive moiety can be the same, or some or all of the reactive moieties may differ. For example, the fluid path can comprise photoreactive groups and chemically reactive. In some embodiments, the fluid path can comprise different photoreactive groups, non limiting examples include, benzophenone and 4-azido-2,3,5,6-tetrafluorobenzoic acid (ATFB).

In addition to the use of photoactivatable chemistry described above, chemical or thermal activation may also be employed.

In some embodiments, the reactive moiety comprises a functional group that can be used to attach the reactive moiety to an analyte by forming a covalent linkage with a complementary group present on the analyte. Pairs of complementary groups capable of forming covalent linkages are well known in the art. In some embodiments, the analyte comprises a nucleophilic group and the reactive group comprises an electrophilic group. In other embodiments, the reactive group comprises a nucleophilic group and the analyte comprises an electrophilic group. Complementary nucleophilic and electrophilic groups, or precursors thereof that can be suitably activated, useful for forming covalent linkages stable in assay conditions are well known and can be used. Examples of suitable complementary nucleophilic and electrophilic groups, as well as the resultant linkages formed therefrom, are provided in U.S. Pat. No. 6,348,596.

In some embodiments, the methods comprise contacting one or more analytes with one or more detection agents. A detection agent is capable of binding to or interacting with the analyte be detected. Contacting the detection agent with the analyte or analytes of interest can be by any method known in the art, so long as it is compatible with the methods and devices described herein. Examples for conveying detection agents through the fluid path include, but are not limited to, hydrodymic flow, electroendosmotic flow, or electrophoresis.

The detection agents can comprise any organic or inorganic molecule capable of binding to interact with the analyte to be detected. Non-limiting examples of detection agents include proteins, peptides, antibodies, enzyme substrates, transition state analogs, cofactors, nucleotides, polynucleotides, aptamers, lectins, small molecules, ligands, inhibitors, drugs, and other biomolecules as well as non-biomolecules capable of binding the analyte to be detected.

In some embodiments, the detection agents comprise one or more label moiety(ies). In embodiments employing two or more label moieties, each label moiety can be the same, or some, or all, of the label moieties may differ.

In some embodiments, the label moiety comprises a chemiluminescent label. The chemiluminescent label can comprise any entity that provides a light signal and that can be used in accordance with the methods and devices described herein. A wide variety of such chemiluminescent labels are known in the art. See, e.g., U.S. Pat. Nos. 6,689,576, 6,395,503, 6,087,188, 6,287,767, 6,165,800, and 6,126,870 the disclosures of which are incorporated herein by reference. Suitable labels include enzymes capable of reacting with a chemiluminescent substrate in such a way that photon emission by chemiluminescence is induced. Such enzymes induce chemiluminescence in other molecules through enzymatic activity. Such enzymes may include peroxidase, beta-galactosidase, phosphatase, or others for which a chemiluminescent substrate is available. In some embodiments, the chemiluminescent label can be selected from any of a variety of classes of luminol label, an isoluminol label, etc. In some embodiments, the detection agents comprise chemiluminescent labeled antibodies.

In some embodiments, the detection agents comprise chemiluminescent substrates. Depending on their charge, the chemiluminescent substrates can be supplied from either end of the fluid path, once the analyte is immobilized in the fluid path. Uncharged substrates can be supplied from either end of the fluid path by hydrodynamic flow or electroendosmotic flow, for example. Chemiluminescent substrates are well known in the art, such as Galacton substrate available from Applied Biosystems of Foster City, Calif. or SuperSignal West Femto Maximum Sensitivity substrate available from Pierce Biotechnology, Inc. of Rockford, Ill. or other suitable substrates.

Likewise, the label moiety can comprise a bioluminescent compound. Bioluminescence is a type of chemiluminescence found in biological systems in which a catalytic protein increases the efficiency of the chemiluminescent reaction. The presence of a bioluminescent compound is determined by detecting the presence of luminescence. Suitable bioluminescent compounds include, but are not limited to luciferin, luciferase and aequorin.

In some embodiments, the label moiety comprises a fluorescent dye. The fluorescent dye can comprise any entity that provides a fluorescent signal and that can be used in accordance with the methods and devices described herein. Typically, the fluorescent dye comprises a resonance-delocalized system or aromatic ring system that absorbs light at a first wavelength and emits fluorescent light at a second wavelength in response to the absorption event. A wide variety of such fluorescent dye molecules are known in the art. For example, fluorescent dyes can be selected from any of a variety of classes of fluorescent compounds, non-limiting examples include xanthenes, rhodamines, fluoresceins, cyanines, phthalocyanines, squaraines, bodipy dyes, coumarins, oxazines, and carbopyronines. In some embodiments, for example, where detection agents contain fluorophores, such as fluorescent dyes, their fluorescence is detected by exciting them with an appropriate light source, and monitoring their fluorescence by a detector sensitive to there characteristic fluorescence emission wavelength. In some embodiments, the detection agents comprise fluorescent dye labeled antibodies.

In embodiments, using two or more different detection agents, which bind to or interact with different analytes, different types of analytes can be detected simultaneously. In some embodiments, two or more different detection agents, which bind to or interact with the one analyte, can be detected simultaneously. In embodiments, using two or more different detection agents, one detection agent, for example a 1° antibody, can bind to or interact with one or more analytes to form a detection agent-analyte complex, and second detection agent, for example a 2° antibody, can be used to bind to or interact with the detection agent-analyte complex.

In some embodiments, two different detection agents, for example antibodies for both phospho- and non-phospho-forms of analyte of interest can enable detection of both forms of the analyte of interest. In some embodiments, a single specific detection agent, for example an antibody, can allow detection and analysis of both phosphorylated and non-phosphorylated forms of a analyte, as these can be resolved in the fluid path. In some embodiments, multiple detection agents can be used with multiple substrates to provide color-multiplexing. For example, the different chemiluminescent substrates used would be selected such that they emit photons of differing color. Selective detection of different colors, as accomplished by using a diffraction grating, prism, series of colored filters, or other means allow determination of which color photons are being emitted at any position along the fluid path, and therefore determination of which detection agents are present at each emitting location. In some embodiments, different chemiluminescent reagents can be supplied sequentially, allowing different bound detection agents to be detected sequentially.

Analyte detection includes detecting of the presence or absence, measurement, and/or characterization of an analyte. Typically, an analyte is detected by detecting a signal from a label and includes, but is not limited, to detecting isotopic labels, immune labels, optical dyes, enzymes, particles and combinations thereof such as chemiluminescent labeled antibodies and fluorescent labeled antibodies.

Detecting the analyte can be by any method known in the art, so long as it is compatible with the methods and devices described herein. Analyte detection can be performed by monitoring a signal using conventional methods and instruments, non-limiting examples include, a photodetector, an array of photodetectors, a charged coupled device (CCD) array, etc. For example, a signal can be a continuously monitored, in real time, to allow the user to rapidly determine whether an analyte is present in the sample, and optionally, the amount or activity of the analyte. In some embodiments, the signal can be measured from at least two different time points. In some embodiments, the signal can be monitored continuously or at several selected time points. Alternatively, the signal can be measured in an end-point embodiment in which a signal is measured after a certain amount of time, and the signal is compared against a control signal (sample without analyte), threshold signal, or standard curve.

A signal can be a monitored, in real time, to allow the user to rapidly determine whether an analyte is present in the sample, and optionally, the amount or activity of the analyte. In some embodiments, the signal can be measured from at least two different time points. In some embodiments, the signal can be monitored continuously or at several selected time points. Alternatively, the signal can be measured in an end-point embodiment in which a signal is measured after a certain amount of time, and the signal is compared against a control signal (sample without analyte), threshold signal, or standard curve.

Typically, detecting the analyte comprises imaging the fluid path. In some embodiments, the entire length of the fluid path can be imaged. Alternatively, a distinct part or portion of the fluid path can be imaged. The amount of the signal generated is not critical and can vary over a broad range. The only requirement is that the signal be measurable by the detection system being used. In some embodiments, a signal can be at least 2-fold greater than the background. In some embodiments, a signal between 2 to 10-fold greater than the background can be generated. In some embodiments, a signal can be 10-fold greater than the background.

The amount of the signal generated is not critical and can vary over a broad range. The only requirement is that the signal be measurable by the detection system being used. In some embodiments, a signal can be at least 2-fold greater than the background. In some embodiments, a signal between 2 to 10-fold greater than the background can be generated. In some embodiments, a signal can be 10-fold greater than the background.

Figure 1A:
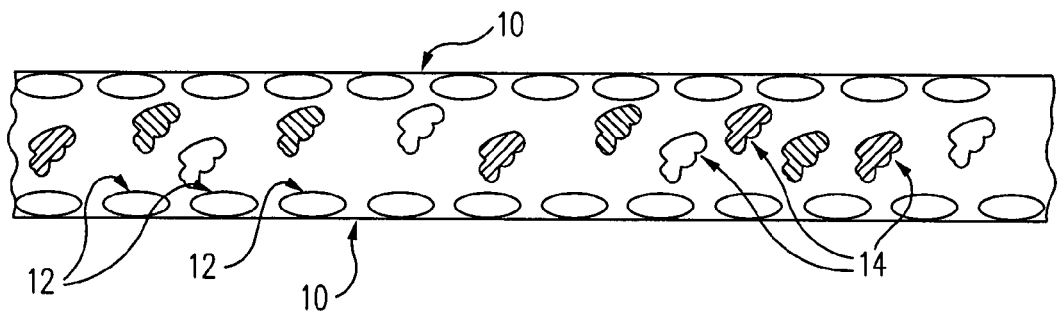
Figure 1B:
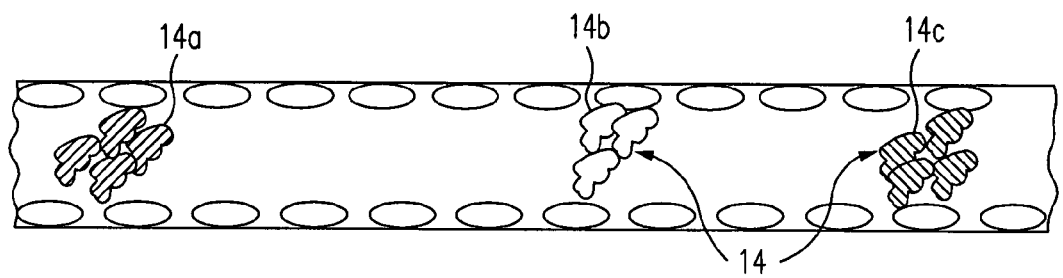
Figure 1C:
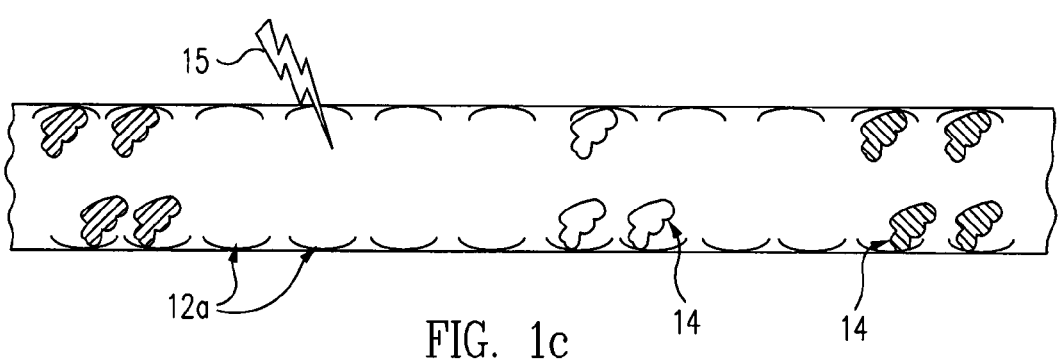
Figure 1D:
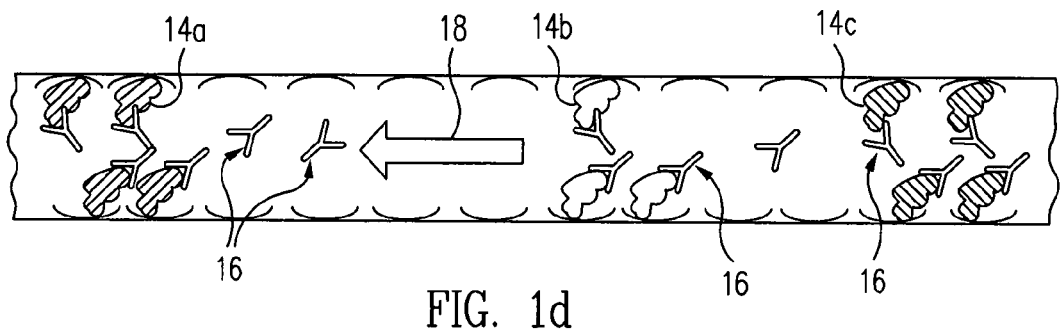

FIG. 1a-d illustrate exemplary embodiments of resolving, immobilizing and labeling cellular materials in a capillary. FIG. 1a is a longitudinal cross-sectional illustration of a capillary 10 which is lined with a photoreactive group 12. Located within a fluid inside the capillary is a mixture of cellular proteins 14 of differing electrophoretic mobility as indicated by the different shading. In FIG. 1b an electric field has been applied to the fluid to separate the proteins in accordance with their isoelectric points by isoelectric focusing (IEF) into groups 14a, 14b, and 14c. In FIG. 1c light 15 at the appropriate wavelength is applied to activate the photoreactive group which, when activated as indicated at 12a, binds the proteins 14 at their separated locations within the capillary. Detection antibodies 16 carrying a label are then flowed through the capillary as indicated by arrow 18 in FIG. 1d. The detection antibodies 16 will bind to the proteins 14 they encounter as shown in FIG. 1d. When the detection antibodies contain chemiluminescent label, the bound proteins are then labeled in their bound locations for luminescent detection. In this embodiment, a stream of chemiluminescence reagents can be flowed through the capillary, reacting when encountering the label linked to the proteins. The luminescence from the sites of the proteins is detected by a photon detector and recorded, enabling identification of the proteins by the light emitted from their bound locations. The technique advantageously permits the identification of cellular materials and, in the case where modification of cellular materials (substrates) is being monitored, allows the use of these native substrates without the need to introduce any identification substances prior to the separation of the cellular materials by IEF.

Generally, the methods described herein yield results similar to those obtained by a Western blot but in a fraction of the time. For example, the separation of cellular materials by IEF can take 5 minutes or less, and subsequent immobilization takes 2 minutes or less. This means that the detection agents can be linked to the separated sample within 10 minutes or less of the commencement of separation, and that the detection agents can be analyzed within 30 minutes of the separating step. The entire process is faster, simpler, more sensitive, more accurate and more automatable than the Western blot analytical technique. The immobilization step obviates the need to assess the detection agents (such as enzyme-labeled antibodies) for homogeneity of molecular form prior to use and obviates the need for excessive purification not typical of these types of reagents. Thus, less costly probing antibodies can be used in the methods described herein.

While the separation technique shown in the previous embodiment is isoelectric focusing, free solution electrophoresis, sieving electrophoresis, or micellar electrokinetic chromatography for example, may also be used to resolve the analytes.

In some embodiments, methods of detecting at least one analyte is provided, comprising, resolving one or more proteins in a fluid path, immobilizing the analytes in the fluid path; and contacting the immobilized analytes with detection agents to form one or more detection agent-analyte complexes in the fluid path, and detecting the analyte. In some embodiments, the detection agent comprises a label. In some embodiments, the method further comprises contacting the detection agent-analyte complex with a labeled detection agent. In some embodiments, the method comprises detecting a chemiluminescent signal. In some embodiments, the method comprises detecting a fluorescent signal.

In some embodiments, methods of detecting at least one protein of interest in a sample are provided, comprising: resolving one or more proteins in a capillary, photoimmobilizing the proteins in the capillary, and contacting the immobilized proteins with antibodies to form one or more antibody-protein complexes in the capillary and detecting the protein. In some embodiments, the antibodies comprise a label. In some embodiments, the method further comprising contacting the antibody-protein complex with a labeled antibody. In some embodiments, the method comprises detecting a chemiluminescent signal. In some embodiments, the method comprises detecting a fluorescent signal.

In some embodiments, methods of detecting at least one analyte in a sample are provided, comprising: resolving one or more analytes in a fluid path, wherein the fluid path comprises one or more reactive groups and, optionally, polymeric or polymerizable materials comprising one or more reactive groups, and immobilizing the analytes in the fluid path and contacting detection agents to the immobilized analytes and detecting the analytes.

Figure 2A:
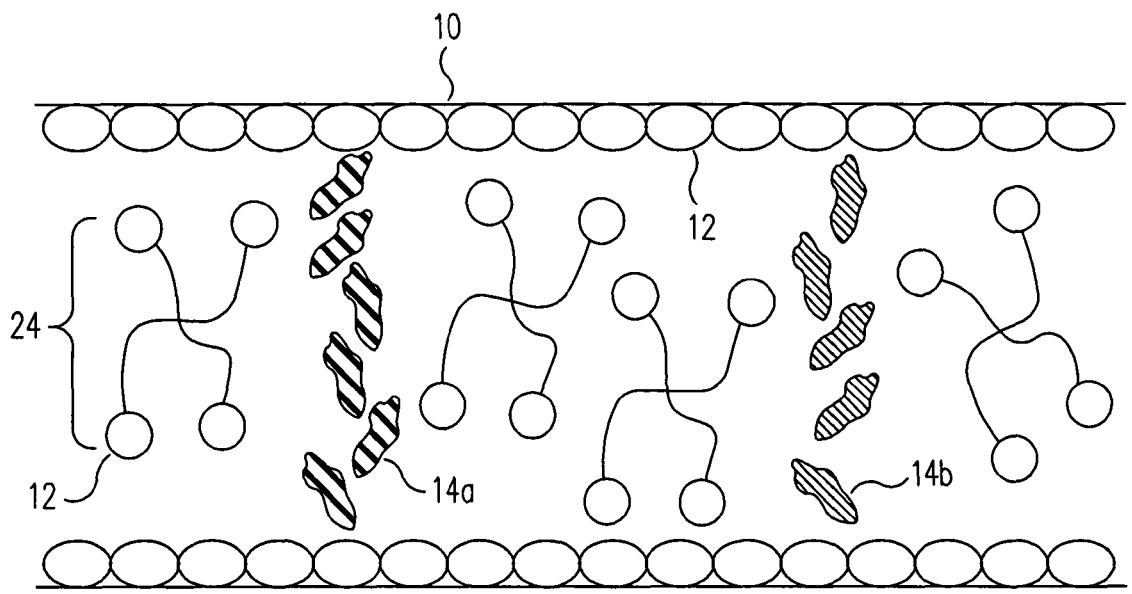
Figure 2B:
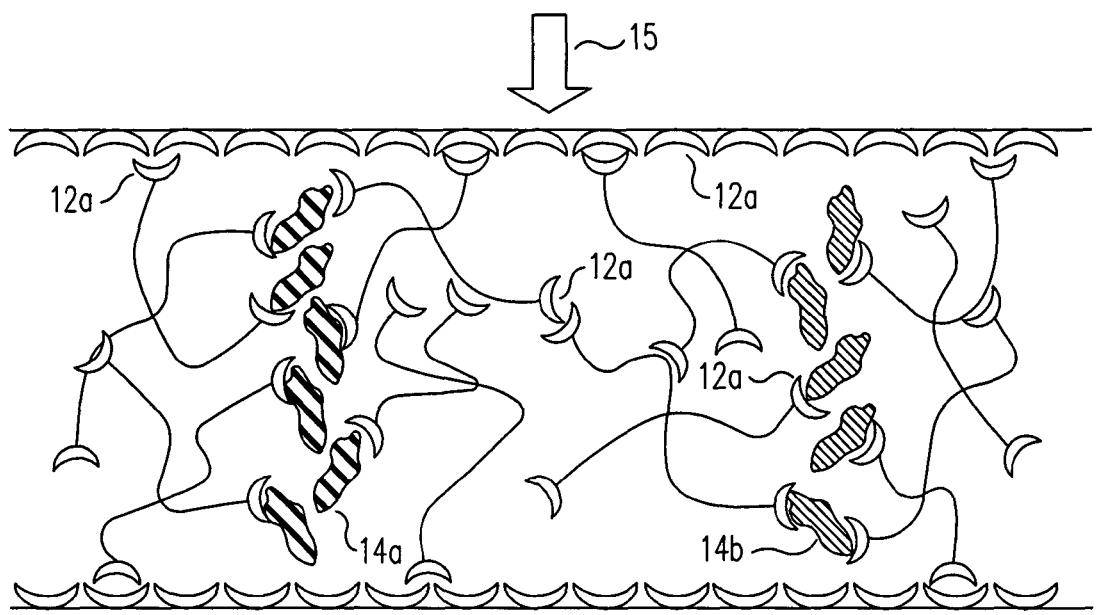

FIG. 2a-b illustrate exemplary embodiments of immobilizing resolved analytes, in a polymeric material in a capillary. FIG. 2a illustrates a longitudinal cross section of a capillary 10. The upper panel shows capillary 10 walls coated on their interior surface with a photoreactive group 12, represented by closed ovals. A suitable, non-limiting example of such material is polyacrylamide containing photoreactive groups, such as benzophenone moieties. Also present in FIG. 2a are polymeric materials 24 in solution, represented by four-armed structures terminated in circles, where the circles represent photoreactive groups 12. A suitable, non-limiting example of such material is branched polyethylene glycol bearing photoreactive groups 12 such as benzophenone, ATFB etc. In addition, two bands of resolved proteins 14a, 14b are shown, represented by the cross-hatched structures. FIG. 2b shows the structures described above after photoactivation 15. Activation of the photoreactive groups is depicted by the concave semicircular structures 12a on both the walls and the polymeric materials filling the capillary. Many of these photoreactive groups 12a are associated with each other, with lengths of polymer, and with the proteins in bands, effectively cross-linking each of these together. Thus, the resolved protein bands are bound in place via a loose network of covalent bonds and polymeric materials. In some embodiments, it is desirable that the network form open-pored structures permitting the movement of materials such as detection agents, such as antibodies, through the loose network.

Figure 3A:
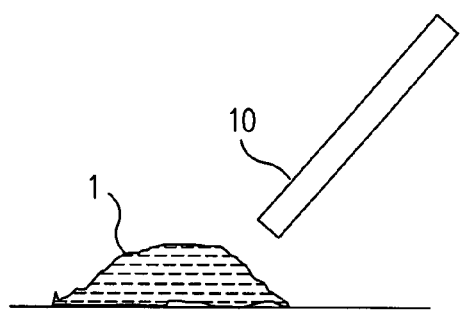
Figure 3B:
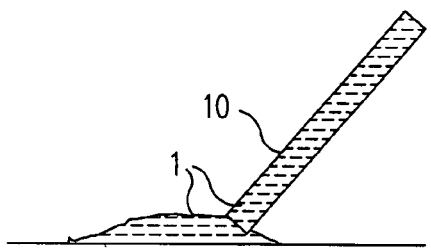
Figure 3C:
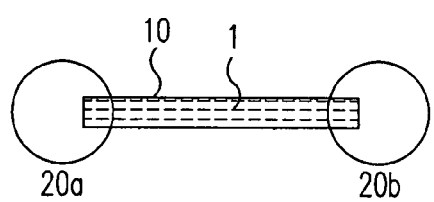
Figure 3D:
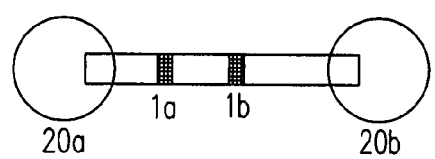
Figure 3F:
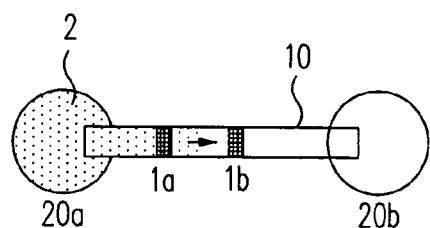
Figure 3E:
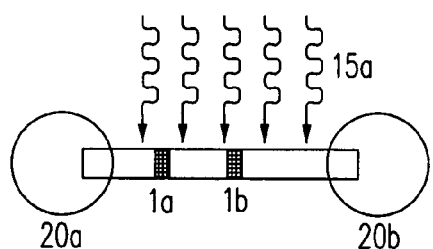
Figure 3G:
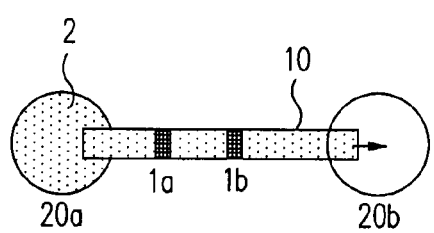
Figure 3H:
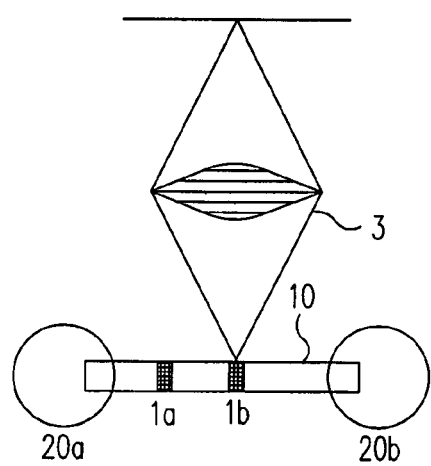

FIGS. 3a-h illustrate exemplary embodiments for detecting one or more analytes in a fluid path. FIG. 3a illustrates a capillary 10 and a sample 1 comprising a mixture of components containing one or more analytes of interest. FIG. 3b illustrates loading the sample 1 into the capillary 10 by capillary action. FIG. 3c illustrates the sample 1 loaded capillary 10, comprising one or more reactive moieties, extending between two fluid-filled wells or troughs 20a, 20b. The components of the sample 1 are separated such that the analyte 1a or analytes 1a and 1b of interests are resolved by one or more electrodes in contact with a solution on one side of the capillary 10 and another one or more electrodes is in contact with a solution on the other side of the capillary 10 as illustrated in FIG. 3d. FIG. 3e illustrates the activation of one or more reactive moieties capable of immobilizing the analytes 1a and 1b of interests in the capillary 10 with light 15a. Detection agents 2 are then flowed through the capillary 10 as indicated by the arrow in FIGS. 3f and 3g. Detection agents 2 are then detected 3, enabling detection of the analyte of interest in their immobilized locations in the capillary by the signal emitted as illustrated in FIG. 3h.

Figure 4:
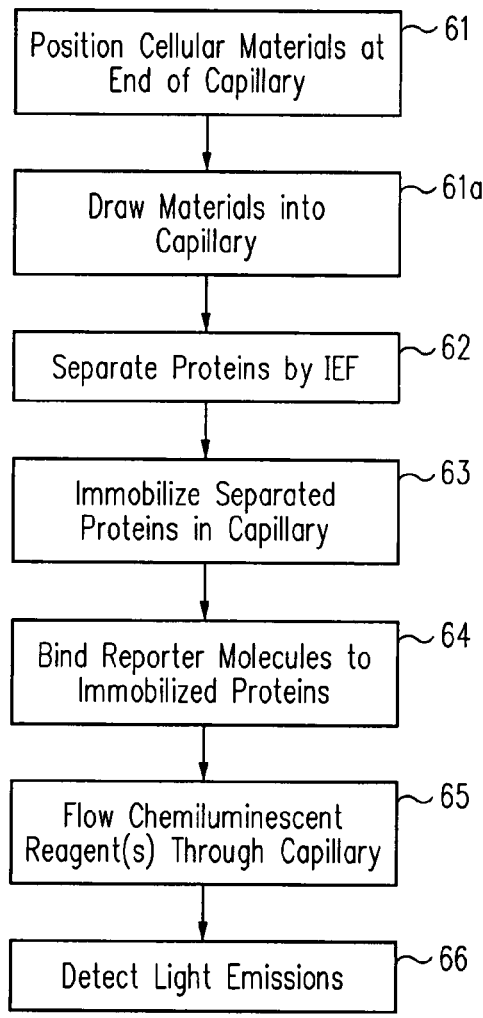
FIG. 4 illustrates an exemplary embodiment of detecting cellular materials.

FIG. 4 illustrates an exemplary embodiment of method for analyzing cellular materials. In step 61 the cellular materials to be analyzed are located at one end of a capillary. In step 61a the cellular materials are loaded in to the capillary. In step 62 the cellular materials are separated within the capillary, for example by IEF. In step 63 the separated materials are immobilized in the capillary. In step 64 detection agents, for example reporter antibodies, are bound to the immobilized analytes, such as proteins in the capillary. In step 65 a chemiluminescent reagents, or other detection agents, are flowed through the capillary to produce the event to be detected, such as chemiluminescence. The emitted light is then detected in step 66.

Figure 5:
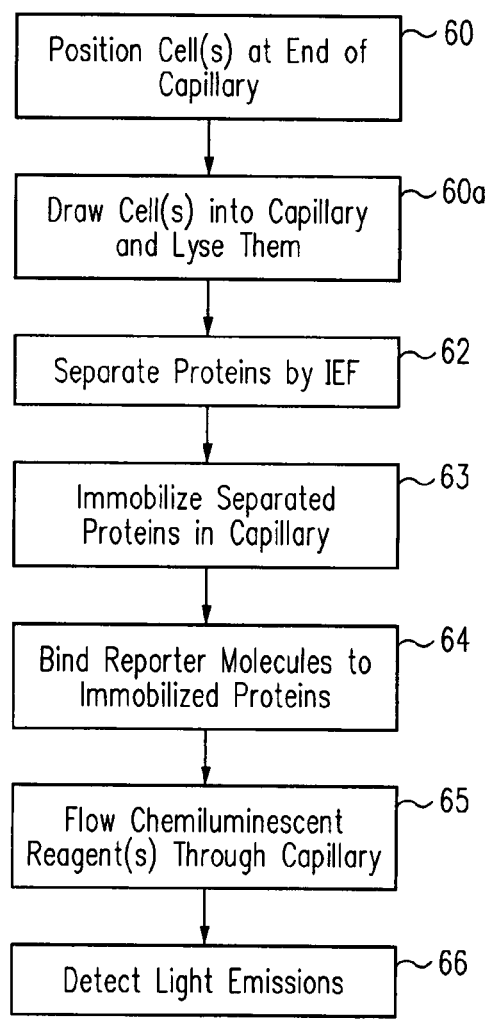
FIG. 5 illustrates an exemplary embodiment of analyzing cell(s).

FIG. 5 illustrates an exemplary embodiment of a method of analyzing cell(s). In step 60 one or more cells to be analyzed are positioned at the end of a capillary. In step 60a one or more cells are drawn into the capillary and are lysed. In step 62 the cellular materials are separated within the capillary, for example by IEF. In step 63 the separated materials are immobilized in the capillary. In step 64 detection agents, for example reporter antibodies, are bound to the immobilized analytes, such as proteins in the capillary. In step 65 a chemiluminescent reagent, or other detection agents, are flowed through the capillary to produce the event to be detected, such as chemiluminescence. The emitted light is then detected in step 66.

Figure 6:
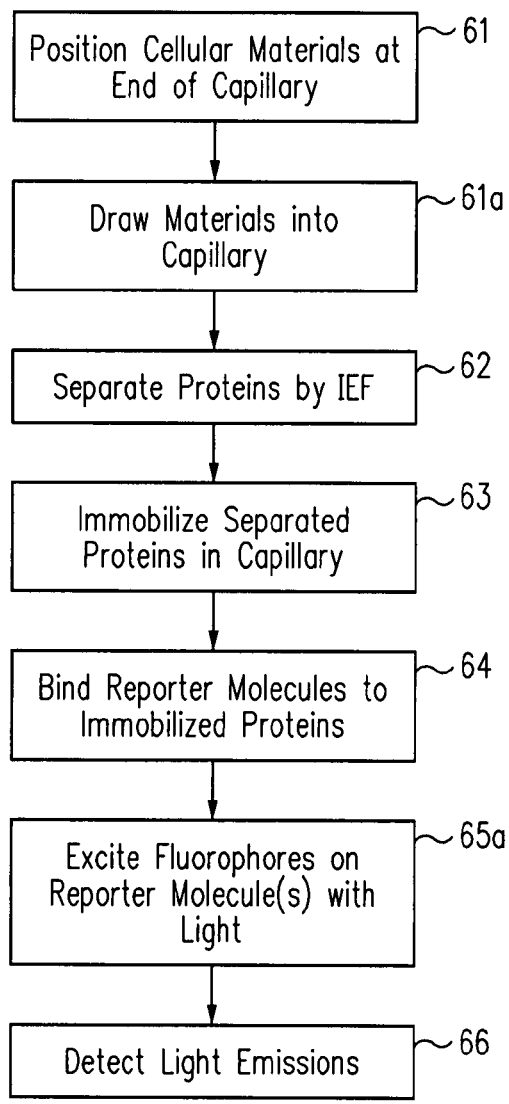
FIG. 6 illustrates an exemplary embodiment of detecting cellular materials.

FIG. 6 illustrates an exemplary embodiment of a method for analyzing cellular materials. In step 61 the cellular materials to be analyzed are located at one end of a capillary. In step 61a the cellular materials are loaded into the capillary. In step 62 the cellular materials are separated within the capillary, for example by IEF. In step 63 the separated materials are immobilized in the capillary. In step 64 detection agents, for example reporter antibodies, are bound to the immobilized analytes, such as proteins in the capillary. In step 65a fluorophores on the detection agents, for example fluorescent labeled antibodies, are excited with light. The emitted light is then detected in step 66.

Figure 7:
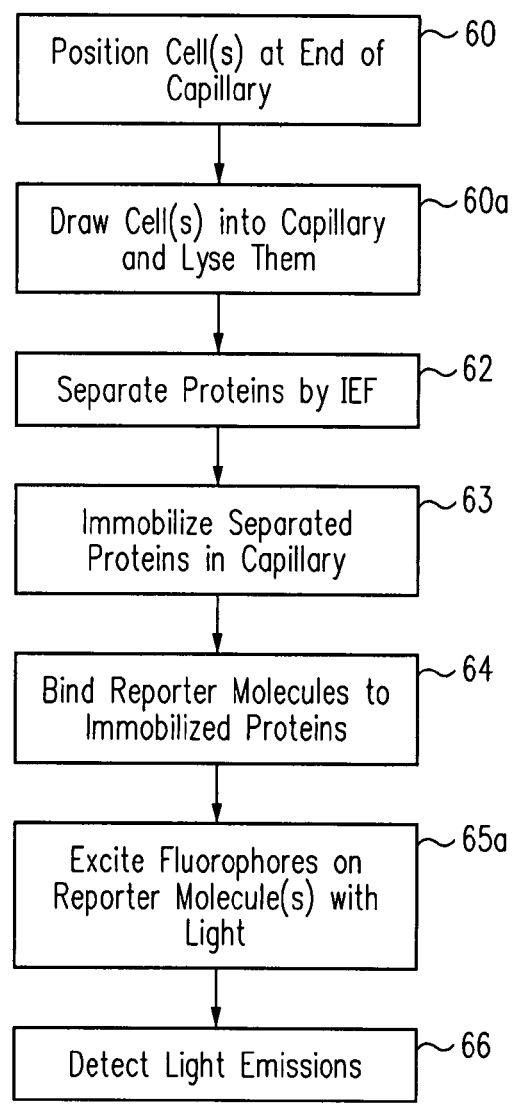
FIG. 7 illustrates an exemplary embodiment of analyzing cell(s).

FIG. 7 illustrates an exemplary embodiment of analyzing cells. In step 60 one or more cells to be analyzed are positioned at the end of a capillary. In step 60a one or more cells are drawn into the capillary and are lysed. In step 62 the cellular materials are separated within the capillary, for example proteins are resolved by IEF. In step 63 the separated materials are immobilized in the capillary. In step 64 detection agents, for example reporter antibodies, are bound to the immobilized analytes, such as proteins in the capillary. In step 65a fluorophores on the detection agents, for example fluorescent labeled antibodies, are exited with light. The emitted light is then detected in step 66.

Figure 8:
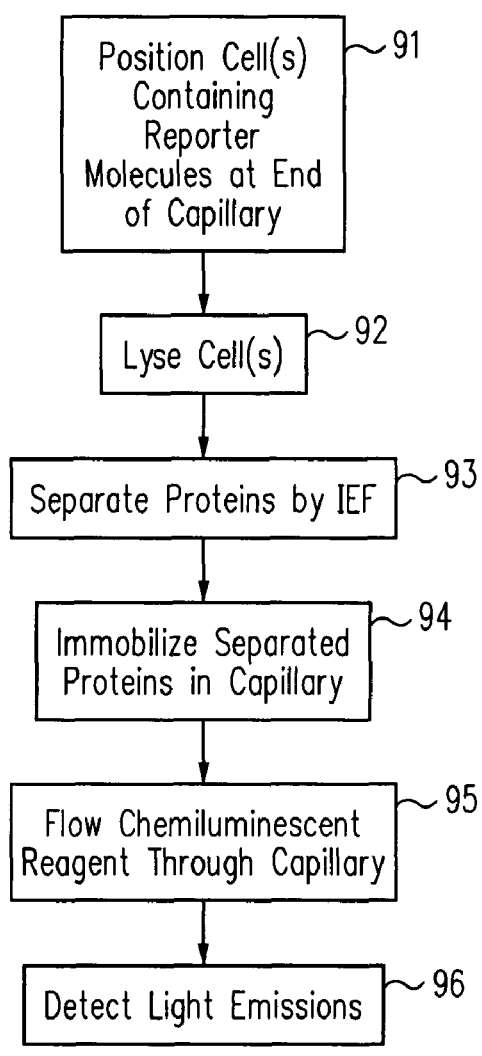
FIG. 8 illustrates an exemplary embodiment of analyzing cell(s).

FIG. 8 illustrates an exemplary embodiment in which labeled cellular materials are released from the cell at the moment of their introduction into the capillary. The cellular materials are then separated and immobilized. In step 91 one or more cells containing detection agents are located at one end of a capillary. The cell or cells are then lysed in step 92 to release their labeled proteins and transported in the capillary. In step 93 the cellular materials are separated, for example within the capillary by IEF. In step 94 the separated materials are immobilized in the capillary. In step 95 a chemiluminescent reagent is then flowed through the capillary to produce photons by chemiluminescence. The emitted photons are then detected in step 96.

Figure 9:
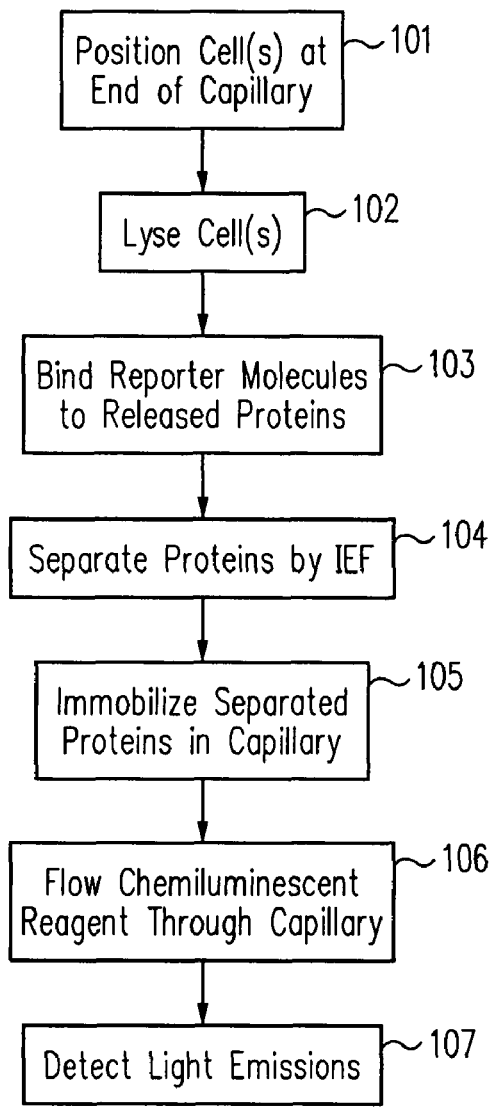
FIG. 9 illustrates an exemplary embodiment of analyzing cell(s).

FIG. 9 illustrates an exemplary embodiment in which analytes are labeled prior to separation. In step 101 one or more cells are located at one end of a capillary. The cell or cells are then lysed in step 102 to release their contents. In step 103 detection agents are bound to the released cellular contents, for example proteins. In step 104 the cellular materials are separated within the capillary by IEF. In step 105 the separated labeled materials are immobilized in place in the capillary. In step 106 a chemiluminescence substrate is then flowed through the capillary to produce photons by chemiluminescence. The emitted photons are then detected in step 107.

Figure 10:
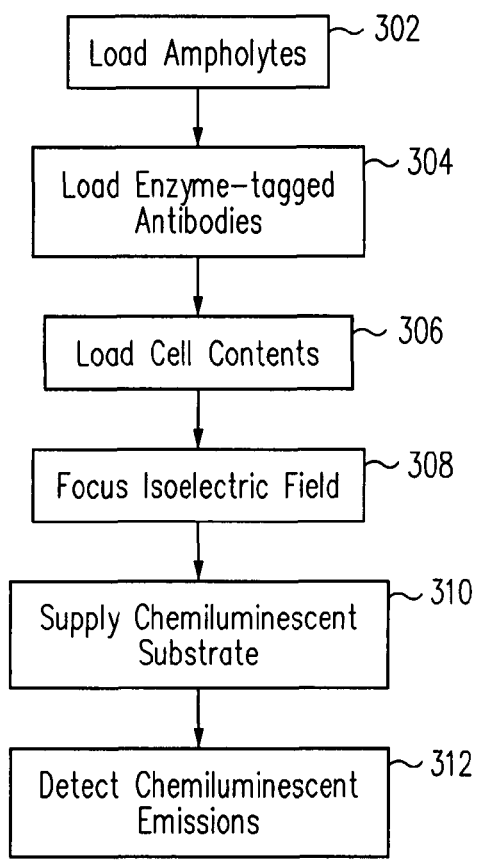
FIG. 10 illustrates an exemplary embodiment of analyzing cellular materials.

FIG. 10 illustrates an exemplary embodiment for chemiluminescent detection of analytes. In step 302 an ampholyte reagent for the pH gradient is loaded into the fluid path. In step 304 enzyme-labeled antibodies able to catalyze chemiluminescence and able to bind the analyte of interest are loaded into the fluid path. The cell contents are loaded into the fluid path in step 306, whereupon the enzyme-tagged antibodies will bind with the analyte or analytes of interest. A focusing isoelectric field is applied in step 308 to resolve and then immobilize the enzyme-tagged antibodies and analytes in a pH gradient. A chemiluminescent substrate compatible with the enzyme-labeled antibodies is supplied in step 310 and chemiluminescent emissions are then detected from the interaction of the chemiluminescent substrate with the enzyme-labeled antibodies and bound to analyte in step 312. In some embodiments, the analyte is immobilized by IEF and the chemiluminescent reagent is flowed through the fluid path by carryings it's own charge at all pH's of the gradient.

Figure 11:
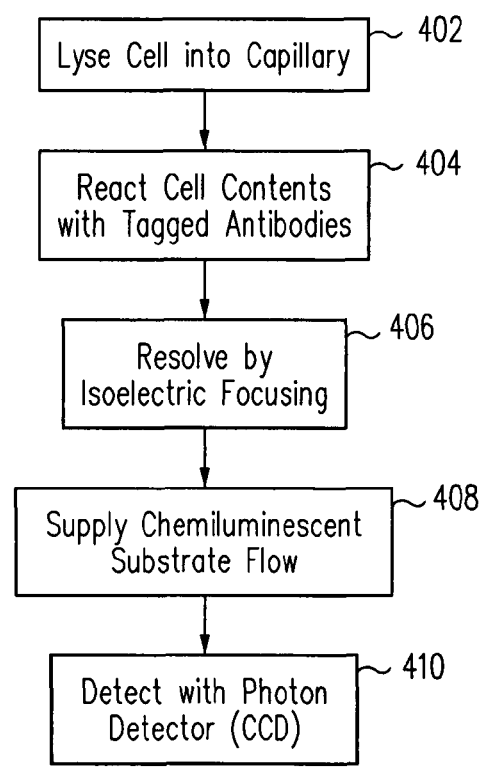
FIG. 11 illustrates an exemplary embodiment of method for analyzing cellular materials.

FIG. 11 illustrates an exemplary embodiment for chemiluminescent detection of analytes. In this embodiment, a cell is lysed into or at the inlet of a capillary in step 402. The lysis releases cellular contents which react with detection agents, for example chemiluminescent labeled antibodies, in step 404. The labeled and bound cellular contents are resolved in the capillary by isoelectric focusing in step 406. In step 408 a chemiluminescent reagent is supplied which will react with the enzyme of the antibodies bound to the cellular contents. In this embodiment, the analyte is immobilized by IEF and the chemiluminescent reagent is flown through the fluid path by carryings it's own charge at all pH's of the gradient. In step 410 chemiluminescence is detected with a photon detector such as a photocell or CCD array detector.

Variations of order of the steps of the methods described herein will readily occur to those skilled in the art. For example, the sample can be separated and then the analyte(s) immobilized at their resolved locations in the fluid path, prior to contacting the analyte(s) with the detection agents. In some embodiments, detection agents are contacted with the analyte(s) to form a complex and then the complex is resolved in the fluid path. In some embodiments, the detection agents could be preloaded into the sample thereafter loaded into the system. As another example, the resolving step, such as isoelectric focusing can be applied after the chemiluminescent reagents are supplied.

Also provided herein are methods of detecting at least one protein in a sample, characterized in that: one or more proteins are resolved from the sample in a capillary and the proteins are photoimmobilized in the capillary and antibodies are conveyed through said capillary which bind to or interact with the proteins or an antibody-protein complex and permit the detecting of the proteins while immobilized in said capillary.

Also, provided herein are methods of detecting at least one protein in a sample, comprising concentrating one or more analytes in a fluid path, immobilizing one or more analytes in the fluid path; and contacting the immobilized analyte with detection agents, and detecting the analyte of interest.

As used herein, concentrating means to make less dilute. Methods of concentrating a sample are well known to those of ordinary skill in the art, and may include, but are not limited to, various kinds of electrophoresis and isoelectric focusing etc.

Also provided are methods of detecting at least one protein in a sample, comprising, concentrating one or more proteins in a fluid path, immobilizing the proteins in the fluid path, and contacting the immobilized protein with antibodies to form one or more antibody-protein complexes in the fluid path, and detecting the protein.

6.3 Devices

Provided herein are systems and devices for detecting one or more analytes in a sample. The device generally comprises a fluid path; a power supply for applying a voltage along the fluid path for separating individual components of a sample in the fluid path; and a detector capable of detecting analyte(s) in the fluid path.

Also provided is a system for detecting at least one analyte of interest in a sample, comprising a fluid path comprising one or more reactive groups capable of immobilizing one or more analytes, a power supply for applying a voltage along the fluid path capable of resolving one or more analytes in the fluid path; and a detector capable of detecting the analyte(s) in said fluid path.

Also provided is a system for detecting at least one analyte of interest in a sample, comprising a fluid path comprising one or more reactive groups capable of immobilizing one or more analytes, a power supply for applying a voltage along the fluid path capable of concentrating one or more analytes in the fluid path; and a detector capable of detecting the analyte(s) in said fluid path.

FIG. 12a illustrates an exemplarily embodiment wherein the fluid path comprises a capillary between fluid filled wells and electrodes. A capillary 10 comprising one or more reactive moieties extends between two fluid-filled wells or troughs 20a, 20b. A sample is placed in one of the troughs, preferably at the orifice of the capillary. For example, the sample can be cellular contents that have been loaded into the capillary. In some embodiments, the one or more cells are drawn into the capillary and lysed in-situ. In some embodiments, one or more cells may be placed in a well, trough or capillary opening and lysed to release the cellular contents. The sample is then flowed through the capillary as by electrophoresis and separated within the capillary, for example by isoelectric focusing. An electrode 22a, 22b is located in the solution at each end of the capillary to apply the electric field necessary for electrophoresis and isoelectric focusing. The detection agents used to label the analyte of interest can be located in the other trough, preferably after separation and immobilization have taken place, and flowed through the capillary by electrophoresis, electroendosmotic flow, or hydrodynamic flow (typically achieved by siphoning or pumping). In some embodiments, the detection agents can be loaded into the capillary from a vessel, such a test tube. The detection agents are then introduced into one of the troughs and flowed through the capillary to elicit the detection events.

FIG. 12b illustrates an exemplary embodiment comprising an array of capillaries 30 extending between a plurality of wells 32a, on one side and another plurality of wells 32b on the other side. In some embodiments an array of capillaries can be extended between a trough, on one side and another trough on the other side. In some embodiments, an array of capillaries can extended between a common buffer reservoir, on one side and another common buffer reservoir on the other side. One or more electrodes 34a is in contact with the solution on one side of the capillaries and another one or more electrodes 34b is in contact with the solution on the other side of the capillaries. A portion of the electrodes may be integral to the reservoir structure. The reservoirs and capillaries are located on or in a substrate 36 such as a slide.

FIG. 13 is an exemplary embodiment, the separation and detection of antibody-analyte complexes within a capillary 122 is illustrated in a longitudinal cross-sectional view of a section of the capillary. Located at positions along the capillary 122 are antibody-analyte complexes 160. Each antibody-analyte complex 160 has a net charge 164 which determines the charge-neutral location 162b to which the complex will migrate. Each complex is located at its charge-neutral location 162a, 162b, 162c in the pH gradient created by isoelectric focusing of the ampholyte reagent. The applied voltage potential focuses the analytes into narrow bands at these isoelectric locations as illustrated in the drawing. Passing through the capillary are chemiluminescent substrates 170 which travel in electrophoretic flow direction 172. When a chemiluminescent substrate 170 encounters a labeled antibody-analyte complex 160 such as a peroxidase enzyme attached to an electrofocused antibody-protein complex, the chemiluminescent substrate is converted to a product plus light. The substrate 170a represents a chemiluminescent substrate which is being converted. The conversion causes light 180 to be emitted by the substrate 170a. Substrate products 170b which result from such conversions continue to flow in the direction of arrow 172. This process continues as long as unconverted chemiluminescent substrates 170 continue to flow through the capillary and encounter new chemiluminescent enzymes with which to react.

FIG. 14 illustrates an exemplary analytical device. An array of capillaries 40 which are loaded with the necessary one or more reactive moieties to immobilize the analytes, buffer, and sample to be analyzed is located in a light-tight box 42. A controllable power supply 46 is coupled to the electrodes on either end of the capillaries to apply the voltages needed to separate the sample and to flow the detection agents and/or chemiluminescent reagents through the capillaries. A voltage is applied to flow the sample into the capillary and to separate the sample, for example by isoelectric focusing. Alternatively, the sample may be loaded into the capillary by hydrodynamic flow and thereafter separated, for example by isoelectric focusing. An energy source (not shown) capable of activating the reactive moieties is provided. For example, a light source such as an ultraviolet lamp provides illumination inside the box to immobilize the individual components of the sample in their separated locations. In some embodiments, the system comprises a light source for induction of fluorescent label. One or more detection agents, such as those described herein, are introduced into the wells at one end of the capillaries and flowed through the capillaries, binding to the analytes. In some embodiments, detection reagent is introduced into the wells and flowed through the capillaries. In some embodiments, detection agents may be introduced from separate smaller wells. Additional smaller wells can be used to conserve dectection agents. Viewing the capillaries within the box 42 to receive the photons emitted from the immobilized analytes and detection molecules is a CCD camera 44. The system is controlled by a computer 48 which switches the power supply 46 and the light, controls the application of detection molecules and reagents, and records and analyzes the photon signals received by the CCD camera 44. Similarly, a light source for induction of fluorescence of molecular standards run in the separation may allow detection with the same CCD camera used to detect chemiluminescence-produced light. Internal standards serve to calibrate the separation with respect to isoelectric point, or for an alternative separation mode, molecular weight. Internal standards for IEF are well know in the art, for example see, Shimura, K., Kamiya, K., Matsumoto, H., and K. Kasai (2002) Fluorescence-Labeled Peptide pI Markers for Capillary Isoelectric Focusing, Analytical Chemistry v74: 1046-1053, and U.S. Pat. No. 5,866,683. Standards to be detected by fluorescence could be illuminated either before or after chemiluminescence, but generally not at the same time as chemiluminescence.

In some embodiments, the analyte and standards are detected by fluorescence. The analyte and standards can each be labeled with fluorescent dyes that are each detectable at discrete emission wavelengths, such that the analyte and standards are independently detectable.

FIG. 15 is an exemplary embodiment in which the photons emitted from the detection molecules are received by a CCD array located beneath the capillary array 40. The CCD array 52 is monitored by a CCD controller 54 which provides amplified received signals to the computer 48.

FIG. 16 illustrates an exemplary embodiment of an analytical device for capillary detection of cellular material by chemiluminescence. The system 110 comprises a microscope 112 having a video ocular readout 114 such as a CCD camera displayed on a CRT screen and/or recorded by a videotape recorder or digital recorder (not shown). In some embodiments, the system allows digital storage of the images and pattern processing in a computer system for automated cell processing and analysis. The CCD video camera system 114 is capable of recording a real time bright field image of a target cell. The device may optionally comprise a cell lysis device 116, such as a laser, sonic generator, electronic pulse generator, or electrodes positioned adjacent to target cell(s) on a cover slip 136. For laser lysis, a pulsed Nd:YAG laser is directed to microscope objective scope 120 of microscope 112. The laser pulse is focused at the interface of the cell chamber cover slip 136 and the buffer solution 154. In the illustrated embodiment, after cell lysis, cell contents are loaded into the end of the capillary by hydrodynamic flow or electrophoresis. In some embodiments, this end of the capillary has already been loaded with a short (few mm or less) slug of labeled antibodies at the time of cell lysis. Thereafter, following a hybridization period, if necessary, separation for example by isoelectric focusing is initiated.

A fused silica capillary 122 is positioned with a micromanipulator (not shown) so that the inlet 126 of capillary 122 is located above the cover slip 136 or slide or microwell plate performed by loading the cell with detection agents prior to lysis or hybridization may be performed in the buffer solution subsequent to lysis. In the latter event, a high concentration of detection agents surrounds or is located adjacent to the cell. One method for achieving the desired high concentration of cell contents in contact with a high concentration of detection agents is to draw the cell contents by hydrodynamic or electrophoretic means into a short length of the capillary adjacent to the capillary end. In this mode this short region of the capillary may be pre-loaded with detection agents from another source such as a tube or well (not shown), or may be drawn into the capillary end along with the cell contents. The distal end 132 or proximal end 126 of capillary 122 is disposed in a solution 134 of chemiluminescent substrates. In some embodiments, resolving and immobilizing the analyte or analytes of interest can occur prior to adding the detection agents. The detection agents are then flowed though the fluid path after the separating the sample and immobilization.

Ampholyte reagent 142 is electrically coupled to a high voltage potential which, when applied to the capillary solution, causes the development of a pH gradient within the capillary 22 by ampholyte migration. A high voltage power supply, such as model CZE 1000R manufactured by Spellman of Plainview, N.Y., which is capable of providing a 20,000 volt potential can be used to maintain the pH gradient in column or capillary 122.

Fused silica capillary 122 may typically exhibit a 100 micron inner diameter and 360 micron outer diameter. The lumen walls can be coated with a neutral coating such as that manufactured by Supelco of Phoenix, Ariz. The coating is used to minimize the electroosmotic flow and thus shorten the migration times for the antibody-target complexes. The total length of the capillary in this embodiment can be as long as 90 to 100 cm, but preferably is considerably shorter, in the range of 10 to 30 cm, or 3 to 6 cm. The cell chamber 136 serves as an inlet reservoir for targeted cell molecules and optionally the ampholyte reagent and chemiluminescent reagent(s) and can be held at ground potential relative to the high voltage potential at the other end of the capillary. In some embodiments either end of the capillary may be at high voltage potential and the other ground, or either end may be positive and the other negative. The outlet reservoir 134 may be held at 15 to 20 kV relative to ground at the proximal end of the capillary, for example. The actual potential used is generally chosen by the desired voltage drop per cm of capillary. Distal outlet 132 of capillary 122 is placed about 5 centimeters below inlet 126 in the case of hydrodynamic loading. For the case of electrophoretic loading, which may be equally or more effective, no particular elevation of the distal end of the capillary is required. Inlet 126 of capillary 122 is used as a micropipette for introducing the cellular contents into capillary 122 after cell lysis. Alternatively, the cell may be drawn intact into the capillary and then lysed in the capillary.

After removing 5 mm of polyimide coating from capillary 122 above inlet 126, inlet 126 is mounted perpendicular to cover slip 136 by a micromanipulator (not shown). The micromanipulator enables precise positioning of the capillary lumen with respect to the target cell to be loaded or lysed and loaded into capillary 122.

Capillary 122 includes an optical observation window 138 through which chemiluminescent or fluorescence events are observed and detected by a CCD array 140 or similar detector. An extended observation window 138 is desirable as it enables the parallel detection of a greater number of events than can be observed through the limited length of a shorter window. Generally the length of the observation window will be chosen in consideration of the length of the CCD array 140 being used. If a non-clear coated capillary is used the polyimide coating of capillary 122 is removed over at least the length of the capillary which opposes the CCD array 140. The observation window 138 is maintained in a fixed position in relation to the CCD array 140 either by mechanical or adhesive means. Preferably the observation window and CCD array are enclosed in darkness so that the only light detected by the CCD array is that emitted by the chemiluminescent or fluorescent events within the capillary. The signals from the detected chemiluminescent or fluorescent events are coupled to a personal computer 144 where they are recorded. In some embodiments the event data may be recorded along with the position in the CCD array at which the event occurred. The data is plotted and total signal corresponding to each focused band calculated using Origin software available from Microcal of North Hampton, Mass., DAX software available from Van Mierlo, Inc. of Eindhoven, The Netherlands, LabVIEW® software available from National Instruments Corp., Austin, Tex., or similar data analysis packages. Data may be presented as a histogram, electropherogram, or other graphical representation, or as a spreadsheet or other numerical format.

In some embodiments, a cell or cells which have not been preloaded with detection agents, the inlet 126 of the capillary 122 is positioned directly above the target cell or cells to be lysed. The cell or cells can be in contact with a high concentration of detection agents, or preferably, a high concentration of detection agents has already been loaded into the capillary end at the time of cell lysis. The lysis device 116 is aimed to create a lysing shock wave or other cell lysing disruption adjacent to the cell or cells. When the lysing pulse is applied the cellular contents are released and the force of the lysing event may aid in propelling the cellular contents into the lumen of the capillary by hydrodynamic flow, electrophoresis, or electroendosmotic flow. Hybridization of the analytes of interest and the detection agents takes place rapidly, either outside the capillary prior to loading of the cell contents, or inside the capillary. The degree of hybridization will be linearly related to the concentrations of the detection agent and the sample. For example, tight-binding (high binding avidity)

antibodies provide molecules which will retain their linking characteristics during capillary transport and isoelectric focusing. Examples of such antibodies are those typically used in ELISA (Enzyme Linked Immuno-Sorbent Assays). Preferably the hybridization is done under non-denaturing conditions. By causing the antibodies and their analytes to be in a natural state, recognition between the antibodies and their target complexes and the chemiluminescent reporters is enhanced. The isoelectric focusing field is applied, causing the antibody-target complexes to migrate to pH points of the pH gradient in the capillary at which their net charge is neutral. The complexes will become stationary in the capillary at pH points where the charge of their molecular components (e.g., phospho, carboxyl, amino, and other charged functional groups) nets out to zero. If forces from flow or diffusion should cause the complexes to drift away from their respective isoelectric points, the gradient field will migrate them back into their charge-neutral positions. The antibody-target complexes are thus resolved along the observation window 138 by capillary isoelectric focusing. In some embodiments, resolving and immobilizing the analyte or analytes of interest can occur prior to adding the detection agents. The detection agents are then flowed though the fluid path after the separating the sample and immobilization.

The electrophoretic potential is then used to cause the chemiluminescent substrate solution 134 to flow through the capillary. This may be initiated at the same time as the electric field which is first applied to establish the pH gradient, or after the gradient has already been established and the antibody-target complexes have been focused. The substrate or substrate(s) are chosen such that they exhibit(s) a net charge at all pH conditions encountered within the capillary so that the substrates do not resolve within the capillary but continue to flow in a continuous stream. As the substrates encounter antibody-target complexes along the capillary they are cleaved by the reporter enzyme of the antibody of the complexes, causing release of photons. Thus, as the stream of chemiluminescent substrate continuously flows through the capillary, the resolved antibody-target complexes will continue to emit photons. Alternatively, an excitation source may be used allowing fluorescence detection. In embodiments where chemiluminescence is used, emission is continuous for as long as the flow of chemiluminescent substrates is promoted, and the noise associated with stray excitation light in fluorescence-based systems is avoided.

The photon emission events are detected by the adjacent CCD array 140 and the detected events accumulated by the computer. Detection and accumulation can be continued for a selected period of time, enabling long detection periods to be used for sensitive detection of very small amounts of targeted cellular molecules. When only a single labeled antibody is used, the number of events accumulated will be a measure of the amount of analytes in the cell or cells used to prepare the lysate. To measure the amounts of different cell proteins or molecules, different antibodies which create different antibody-target complexes at different isoelectric points can be employed. By recording the number of photon events and the locations along the CCD array at which the events were detected (corresponding to the focused bands or isoelectric points along the gradient field of the capillary) the photon events emanating from the differently labeled analytes can be segmented. For increased throughput, multiple parallel capillaries or channels can be run past one or more CCD arrays incorporated into a single instrument. In another embodiment, multiple antibodies labeled with different fluorescent dyes having spectrally resolvable signals can be used to enable multiplexed analysis of different proteins in a single capillary.

Fluorescent standards can be read separately if desired, using the same detector before or after the chemiluminescence signals have been collected, by exposing the fluors to excitation light. For an all fluorescence system, the analyte and standards can be discerned by using differentially excitable and detectable dyes.

While the CCD array is preferred for its ability to detect in parallel the photon events occurring along the array, it is understood that more restricted detection techniques may be acceptable in a given embodiment. For instance, a single photon sensor may be swept or moved along the observation window 138 to detect the chemiluminescent or fluorescent photon events. This approach, however, may miss an event at one point of the capillary when the sensor is aimed or located at a different point of the capillary. Furthermore the use of an designed for commonly available fixed window location capillary electrophoresis instruments, resolution can be deteriorated by laminar flow within the capillary, and chemiluminescent or fluorescent sensitivity would be reduced due to the limited time that a photon source is in the observation window.

6.4 Kits

Also provided are kits for performing the methods, and for use with the systems and devices of the present teachings. Materials used in the present invention include but are not limited to a fluid path, capillaries, buffer, detection agents, one or more reactive moieties, polymeric or polymerizable materials comprising one or more reactive moieties; chemiluminescent substrates, blocking solutions, and washing solutions. In some embodiments, the kit can further comprise immobilization agents, ampholytes, and one or more reactive moieties. In some embodiments, the kit can further comprise chemicals for the activation of the reactive moiety. These other components can be provided separately from each other, or mixed together in dry or liquid form.

7. EXAMPLES

Aspects of the present teachings may be further understood in light of the following examples, which should not be construed as limiting the scope of the present teachings in any way.

7.1 Example 1

Fluorescence Detection of Green Fluorescent Protein (GFP)

Preparation of GFP sample for analysis: In a microcentrifuge tube, 40 µL. of DI water, 1 µL of GFP at 1 mg/ml (Part number 632373, Beckton-Dickinson, San Jose, Calif., USA), 5 µL of bioPLUS pI 4-7 (Bio-World, Dublin, Ohio), and 2 µL of ATFB-PEG cross-linking agent (2 mM) were combined. The ATFB-PEG cross-linking agent consists of 15,000 MW branched polyethylene glycol (product number P4AM-15, SunBio, Anyang City, South Korea) in which each branch terminus was derivatized with an ATFB (4-azido-2,3,5,6-tetrafluorobenzoic acid) functionality (product number A-2252, Invitrogen Corporation, Carlsbad, Calif.).

Preparation of capillary: 100µ I.D.×375µ O.D. Teflon-coated fused silica capillary with interior vinyl coating (product number 0100CEL-01, Polymicro Technologies, Phoenix, Ariz.) was surface grafted on its interior with polyacrylamide containing 1 mole percent benzophenone. 4 cm sections of this capillary material were cleaved from longer lengths and used as described below.

Sample loading into capillary: The sample as prepared above was loaded into sections of capillary prepared as described above by touching the tip of the empty capillary to the sample as illustrated in FIG. 3b. Capillary action was sufficient to completely fill the capillary in less than five seconds.

Separation by isoelectric focusing (IEF): Capillaries loaded as described above were placed in a capillary holder as illustrated in FIG. 12b. A 20 mM NaOH solution was placed in the cathode end and a 10 mM $H_3PO_4$ solution was placed in the anode end of the holder, in contact with the electrodes and capillaries, A potential of 300 V was then applied for 900 seconds to facilitate isoelectric focusing, which is often achieved within the first few minutes of this period. GFP was resolved in a 4-7 pI gradient.

Immobilization by ultraviolet light: After the focusing period the capillaries were irradiated for 30 seconds with UV light using an 1800 Watt F300S lamp (Fusion Systems, Inc., Gaithersburg, Md.) at 5 inches distance from the capillaries to cause photo-crosslinking.

Washing, blocking and probing step: After immobilization as described above, the capillaries were removed from the capillary holder and the anodic end of each capillary was placed in contact with a TBST solution consisting of 10 mM Tris-HCl, 150 mM NaCl, 0.05% Tween 20, pH 6.8. A ≧5 mmHg vacuum source was applied to the cathodic end of each capillary and TBST solution was pulled through each capillary for 5 minutes. Using the same ≧5 mmHg vacuum source and capillary orientation, a 5% powdered skim milk solution (w/v) in TBST was pulled through each capillary for 20 minutes. Fluorescent dye labeled primary antibody solution (1:1000 dilution of Alexa-555-labeled rabbit anti-GFP, Part number A-31851, Molecular Probes, Eugene, Oreg., USA in 5% milk in TBST) was then introduced to each capillary using the same vacuum source applied for 2 minutes, followed by 10 minutes incubation with vacuum off. This antibody application procedure was repeated a total of 5 times. Then, the same approach was used to flush the capillary with 5% milk solution in TBST for 20 minutes. Finally the capillaries were flushed for 5 minutes with TBST, and then 2 minutes TBS (10 mM Tris-HCl, 150 mM NaCl).

Detection by fluorescence: For fluorescence detection, capillaries were read using a Molecular Dynamics Avalanche™ scanner with excitation at 532 nm and emission detection at 575 nm. The relative fluorescence units along the length of the capillary as pixel number is shown in FIG. 17. The pixel number scale in FIGS. 17-22 varies because of different CCDs and positioning relative to the capillary.

7.2 Example 2

Chemiluminescence Detection of GFP

Preparation of GFP sample for analysis: In a microcentrifuge tube, 40 µL of DI water, 1 µL of GFP at 1 mg/ml (Part number 632373, BD Biosciences, San Jose, Calif., USA), 5 µL of bioPLUS pI 4-7 (Bio-World, Dublin, Ohio), and 2 µL of ATFB-PEG cross-linking agent (2 mM) were combined. The ATFB-PEG cross-linking agent consists of 15,000 MW branched polyethylene glycol (product number P4AM-15, SunBio, Anyang City, South Korea) in which each branch terminus was derivatized with an ATFB (4-azido-2,3,5,6-tetrafluorobenzoic acid) functionality (product number A-2252, Invitrogen Corporation, Carlsbad, Calif.).

Preparation of capillary: 100µ I.D.×375µ O.D. Teflon-coated fused silica capillary with interior vinyl coating (product number 0100CEL-01, Polymicro Technologies, Phoenix, Ariz.) was surface grafted on its interior with polyacrylamide containing 1 mole percent benzophenone. 4 cm sections of this capillary material were cleaved from longer lengths and used as described below.

Sample loading into capillary: The sample as prepared above was loaded into sections of capillary prepared as described above by touching the tip of the empty capillary to the sample as illustrated in FIG. 3b. Capillary action was sufficient to completely fill the capillary in less than five seconds.

Separation by isoelectric focusing (IEF): Capillaries loaded as described above were placed in a capillary holder as illustrated in FIG. 12b. A 20 mM NaOH solution was placed in the cathode end and a 10 mM $H_3PO_4$ solution was placed in the anode end of the holder, in contact with the electrodes and capillaries. A potential of 300 V was then applied for 900 seconds to facilitate isoelectric focusing, which is often achieved within the first few minutes of this period. GFP was resolved in a 4-7 pI gradient.

Immobilization by ultraviolet light: After the focusing period the capillaries were irradiated for 30 seconds with UV light using an 1800 Watt F300S lamp (Fusion Systems, Inc., Gaithersburg, Md.) at 5 inches distance from the capillaries to cause photo-crosslinking.

Washing, blocking and probing step: After immobilization as described above, the capillaries were removed from the capillary holder and the anodic end of each capillary was placed in contact with a TBST solution consisting of 10 mM Tris-HCl, 150 mM NaCl, 0.05% Tween 20, pH 6.8. A ≧5 mmHg vacuum source was applied to the cathodic end of each capillary and TBST solution was pulled through each capillary for 5 minutes. Using the same ≧5 mmHg vacuum source and capillary orientation, a 5% powdered skim milk solution (w/v) in TBST was pulled through each capillary for 20 minutes. Primary antibody solution (1:1000 dilution of rabbit anti-GFP, Part number A-11122, Molecular Probes, Eugene, Oreg., USA, in 5% milk in TBST) was then introduced to each capillary using the same vacuum source applied for 2 minutes, followed by 10 minutes incubation with vacuum off. This antibody application procedure was repeated a total of 5 times. Then, the same approach was used to flush the capillary with 5% milk solution in TBST for 20 minutes. A secondary (2°) antibody solution was then applied (1:10,000 anti-rabbit HRP in 5% milk in TBST, Cat# 81-6120, Zymed, South San Francisco, Calif.), again by flowing antibody solution for 2 minutes with vacuum on followed by 10 minutes of incubation with vacuum off, repeating a total of 5 times. The capillaries were then again flushed with a 5% milk solution in TBST for 20 minutes. Finally the capillaries were flushed for 5 minutes with TBST, and then 2 minutes TBS (10 mM Tris-HCl, 150 mM NaCl).

Detection by chemiluminescence: For chemiluminescence detection, a mixture of equal parts of SuperSignal West Femto Stable Peroxide buffer (Cat#1859023, Pierce, Rockford, Ill.) and Luminol/Enhancer solution (Cat#1859022, Pierce, Rockford, Ill.) was supplied to the capillaries and flushed through with 5 mmHg vacuum. Chemiluminescence signal was collected for 60 seconds using a CCD camera in a prototype chemiluminescence detection module produced by Cell Biosciences, U.S. Patent Application No. 60/669,694 filed Apr. 9, 2005. The relative luminescence signal along the length of a capillary as pixel number is shown in FIG. 18.

7.3 Example 3

Fluorescent Detection of Horse Myoglobin

Preparation of protein sample: was prepared at 20 µg/ml in ** buffer and stored at 4° C. until use, or frozen at −70° C. for long-term storage.

Preparation of sample for analysis: In a microcentrifuge tube, 40 µL of DI water, 2 µL of 4 mg/ml purified horse myoglobin (Part number M-9267, Sigma-Aldrich, St. Louis, Mo., USA) myoglobin solution, 5 µL of Pharmalyte ampholyte pI 3-10 (Sigma, St. Louis), and 2 µL of ATFB-PEG cross-linking agent (2 mM) were combined. The ATFB-PEG cross-linking agent consists of 15,000 MW branched polyethylene glycol (product number P4AM-15, SunBio, Anyang City, South Korea) in which each branch terminus was derivatized with an ATFB (4-azido-2,3,5,6-tetrafluorobenzoic acid) functionality (product number A-2252, Invitrogen Corporation, Carlsbad, Calif.).

Preparation of capillary: 100µ I.D.×375µ O.D. Teflon-coated fused silica capillary with interior vinyl coating (product number 0100CEL-01, Polymicro Technologies, Phoenix, Ariz.) was surface grafted on its interior with polyacrylamide containing 1 mole percent benzophenone. 4 cm sections of this capillary material were cleaved from longer lengths and used as described below.

Sample loading into capillary: The sample as prepared above was loaded into sections of capillary prepared as described above by touching the tip of the empty capillary to the sample as illustrated in FIG. 3b. Capillary action was sufficient to completely fill the capillary in less than five seconds.

Separation by isoelectricfocusing (IEF): Capillaries loaded as described above were placed in a capillary holder as illustrated in FIG. 12b. A 20 mM NaOH solution was placed in the cathode end and a 10 mM $H_3PO_4$ solution was placed in the anode end of the holder, in contact with the electrodes and capillaries. A potential of 300 V was then applied for 900 seconds to facilitate isoelectric focusing, which is often achieved within the first few minutes of this period. Horse myoglobin was resolved in a 3-10 pI gradient.

Immobilization by ultraviolet light: After the focusing period the capillaries were irradiated for 30 seconds with UV light using an 1800 Watt F300S lamp (Fusion Systems, Inc., Gaithersburg, Md.) at 5 inches distance from the capillaries to cause photo-crosslinking.

Washing, blocking and probing step: After immobilization as described above, the capillaries were removed from the capillary holder and the anodic end of each capillary was placed in contact with a TBST solution consisting of 10 mM Tris-HCl, 150 mM NaCl, 0.05% Tween 20, pH 6.8. A ≧5 mmHg vacuum source was applied to the cathodic end of each capillary and TBST solution was pulled through each capillary for 5 minutes. Using the same ≧5 mmHg vacuum source and capillary orientation, a 5% powdered skim milk solution (w/v) in TBST was pulled through each capillary for 20 minutes. Fluorescent labeling of goat anti-horse myoglobin primary antibody (part number A150-103A, Bethyl Labs, Montgomery, Tex.) was performed by NHS ester coupling chemistry with Alexa-647 dye (part number A20006, Molecular Probes, Eugene, Oreg.). The primary antibody solution (1:50 dilution of Alexa-647-labeled goat anti-horse myoglobin in 5% milk in TBST) was then introduced to each capillary using the same vacuum source applied for 2 minutes, followed by 10 minutes incubation with vacuum off. This antibody application procedure was repeated a total of 5 times. Then, the same approach was used to flush the capillary with 5% milk solution in TBST for 20 minutes. Finally the capillaries were flushed for 5 minutes with TBST, and then 2 minutes TBS (10 mM Tris-HCl, 150 mM NaCl).

Detection by fluorescence: For fluorescence detection, capillaries were read using a Molecular Dynamics Avalanche™ scanner with excitation at 633 nm and emission detection at 675 nm. The relative fluorescence units along the length of a capillary as pixel number is shown in FIG. 19.

7.4 Example 4

Chemiluminescence Detection of Akt Protein from LNCaP Cell Lysate Sample

Preparation of cell lysate: Cell lysate was prepared for analysis by lysing $1 \times 10^6$ LNCaP cells (Human prostate cancer cell line) in one ml of 4° C. HNTG lysis buffer (20 mM HEPES pH 7.5, 150 mM NaCl, 0.1% Triton-X 100, 10% Glycerol). The resulting lysate was clarified of insoluble cellular debris through centrifugation at 11,000 g for 15 min. at 4° C. The supernatant was decanted to a fresh tube and stored at 4° C. until use, or frozen at −70° C. for long-term storage.

Preparation of lysate sample for analysis: In a microcentrifuge tube, 40 µL of DI water, 50 µL of cell lysate, 5 µL of bioPLUS pI 4-7 (Bio-World, Dublin, Ohio), and 2 µL of ATFB-PEG cross-linking agent (2 mM) were combined. The ATFB-PEG cross-linking agent consists of 15,000 MW branched polyethylene glycol (product number P4AM-15, SunBio, Anyang City, South Korea) in which each branch terminus was derivatized with an ATFB (4-azido-2,3,5,6-tetrafluorobenzoic acid) functionality (product number A-2252, Invitrogen Corporation, Carlsbad, Calif.).

Preparation of capillary: 100µ I.D.×375µ O.D. Teflon-coated fused silica capillary with interior vinyl coating (product number 0100CEL-01, Polymicro Technologies, Phoenix, Ariz.) was surface grafted on its interior with polyacrylamide containing 1 mole percent benzophenone. 4 cm sections of this capillary material were cleaved from. longer lengths and used as described below.

Sample loading into capillary: The sample as prepared above was loaded into sections of capillary prepared as described above by touching the tip of the empty capillary to the sample as illustrated in FIG. 3b. Capillary action was sufficient to completely fill the capillary in less than five seconds.

Separation by isoelectric focusing (IEF): Capillaries loaded as described above were placed in a capillary holder as illustrated in FIG. 12b. A 20 mM NaOH solution was placed in the cathode end and a 10 mM $H_3PO_4$ solution was placed in the anode end of the holder, in contact with the electrodes and capillaries. A potential of 300 V was then applied for 900 seconds to facilitate isoelectric focusing, which is often achieved within the first few minutes of this period. Akt was resolved in a 4-7 pI gradient.

Immobilization by ultraviolet light: After the focusing period the capillaries were irradiated for 30 seconds with UV light using an 1800 Watt F300S lamp (Fusion Systems, Inc., Gaithersburg, Md.) at 5 inches distance from the capillaries to cause photo-crosslinking.

Washing, blocking and probing step: After immobilization as described above, the capillaries were removed from the capillary holder and the anodic end of each capillary was placed in contact with a TBST solution consisting of 10 mM Tris-HCl, 150 mM NaCl, 0.05% Tween 20, pH 6.8. A ≧5 mmHg vacuum source was applied to the cathodic end of each capillary and TBST solution was pulled through each capillary for 5 minutes. Using the same ≧5 mmHg vacuum source and capillary orientation, a 5% powdered skim milk solution (w/v) in TBST was pulled through each capillary for 20 minutes. Primary antibody solution (1:100 dilution of rabbit anti-AKT, sc8312, Santa Cruz Biotechnology, Santa Cruz, Calif., in 5% milk in TBST) was then introduced to each capillary using the same vacuum source applied for 2 minutes, followed by 10 minutes incubation with vacuum off. This antibody application procedure was repeated a total of 5 times. Then, the same approach was used to flush the capillary with 5% milk solution in TBST for 20 minutes. A secondary (2°) antibody solution was then applied (1:10,000 anti-rabbit HRP in 5% milk in TBST, Cat# 81-6120, Zymed, South San Francisco, Calif.), again by flowing antibody solution for 2 minutes with vacuum on followed by 10 minutes of incubation with vacuum off, repeating a total of 5 times. The capillaries were then again flushed with a 5% milk solution in TBST for 20 minutes. Finally the capillaries were flushed for 5 minutes with TBST, and then 2 minutes TBS (10 mM Tris-HCl, 150 mM NaCl).

Detection by chemiluminescence: For chemiluminescence detection, a mixture of equal parts of SuperSignal® West Femto Stable Peroxide buffer (Cat#1859023, Pierce, Rockford, Ill.) and Luminol/Enhancer solution (Cat#1859022, Pierce, Rockford, Ill.) was supplied to the capillaries and flushed through with 5 mmHg vacuum. Chemiluminescence signal was collected for 60 seconds using a CCD camera in a prototype chemiluminescence detection module produced by Cell Biosciences U.S. Patent Application 60/669,694 filed Apr. 9, 2005. The relative luminescence signal along the length of a capillary as pixel number is shown in FIG. 20 and the upper panel of FIG. 22.

7.5 Example 5

Chemiluminescence Detection of Akt Protein from LNCaP Cell Lysate Using Anti-Phospho-S473-Antibody Preparation of cell lysate: Cell lysate was prepared for analysis by lysing $1 \times 10^6$ LNCaP cells (Human prostate cancer cell line) in one ml of 4° C. HNTG lysis buffer (20 mM HEPES pH 7.5, 150 mM NaCl, 0.1% Triton-X 100, 10% Glycerol). The resulting lysate was clarified of insoluble cellular debris through centrifugation at 11,000 g for 15 min. at 4° C. The supernatant was decanted to a fresh tube and stored at 4° C. until use, or frozen at −70° C. for long-term storage.

Preparation of lysate sample for analysis: In a microcentrifuge tube, 40 µL of DI water, 50 µL of cell lysate, 5 µL of Pharmalyte ampholyte pI 3-10 (Sigma, St. Louis), and 2 µL of ATFB-PEG cross-linking agent (2 mM) were combined. The ATFB-PEG cross-linking agent consists of 15,000 MW branched polyethylene glycol (product number P4AM-15, SunBio, Anyang City, South Korea) in which each branch terminus was derivatized with an ATFB (4-azido-2,3,5,6-tetrafluorobenzoic acid) functionality (product number A-2252, Invitrogen Corporation, Carlsbad, Calif.).

Preparation of capillary: 100µ I.D.×375µ O.D. Teflon-coated fused silica capillary with interior vinyl coating (product number 0100CEL-01, Polymicro Technologies, Phoenix, Ariz.) was surface grafted on its interior with polyacrylamide containing 1 mole percent benzophenone. 4 cm sections of this capillary material were cleaved from longer lengths and used as described below.

Sample loading into capillary: The sample as prepared above was loaded into sections of capillary prepared as described above by touching the tip of the empty capillary to the sample as illustrated in FIG. 3b. Capillary action was sufficient to completely fill the capillary in less than five seconds.

Separation by isoelectric focusing (IEF): Capillaries loaded as described above were placed in a capillary holder as illustrated in FIG. 12b. A 20 mM NaOH solution was placed in the cathode end and a 10 mM $H_3PO_4$ solution was placed in the anode end of the holder, in contact with the electrodes and capillaries. A potential of 300 V was then applied for 900 seconds to facilitate isoelectric focusing, which is often achieved within the first few minutes of this period. Protein was resolved in a 4-7 pI gradient Immobilization by ultraviolet light: After the focusing period the capillaries were irradiated for 30 seconds with UV light using an 1800 Watt F300S lamp (Fusion Systems, Inc., Gaithersburg, Md.) at 5 inches distance from the capillaries to cause photo-crosslinking.

Washing, blocking and probing step: After immobilization as described above, the capillaries were removed from the capillary holder and the anodic end of each capillary was placed in contact with a TBST solution consisting of 10 mM Tris-HCl, 150 mM NaCl, 0.05% Tween 20, pH 6.8. A $\geq 5$ mmHg vacuum source was applied to the cathodic end of each capillary and TBST solution was pulled through each capillary for 5 minutes. Using the same $\geq 5$ mmHg vacuum source and capillary orientation, a 5% powdered skim milk solution (w/v) in TBST was pulled through each capillary for 20 minutes. Primary antibody solution (1:100 dilution of rabbit anti-phospho-S473 AKT, Part number 4051, Cell Signaling Technologies, Beverly, Mass., USA, in 5% milk in TBST) was then introduced to each capillary using the same vacuum source applied for 2 minutes, followed by 10 minutes incubation with vacuum off. This antibody application procedure was repeated a total of 5 times. Then, the same approach was used to flush the capillary with 5% milk solution in TBST for 20 minutes. A secondary (2°) antibody solution was then applied (1:10,000 anti-rabbit HRP in 5% milk in TBST, Cat# 81-6120, Zymed, South San Francisco, Calif.), again by flowing antibody solution for 2 minutes with vacuum on followed by 10 minutes of incubation with vacuum off, repeating a total of 5 times. The capillaries were then again flushed with a 5% milk solution in TBST for 20 minutes. Finally the capillaries were flushed for 5 minutes with TBST, and then 2 minutes TBS (10 mM Tris-HCl, 150 mM NaCl).

Detection by chemiluminescence: For chemiluminescence detection, a mixture of equal parts of SuperSignal West Femto Stable Peroxide buffer (Cat#1859023, Pierce, Rockford, Ill.) and Luminol/Enhancer solution (Cat#1859022, Pierce, Rockford, Ill.) was supplied to the capillaries and flushed through with 5 mmHg vacuum. Chemiluminescence signal was collected for 60 seconds using a CCD camera in a prototype chemiluminescence detection module produced by Cell Biosciences, U.S. Patent Application No. 60/669,694 filed Apr. 9, 2005. The relative luminescence signal along the length of a capillary as pixel number is shown in FIG. 21 and the lower panel of FIG. 22.

FIG. 22 compares the chemiluminescence signals generated in FIGS. 21 and 22 illustrating the resolving of phosphorylated and non-phosphorylated forms of the Akt protein by a single, total-protein-specific antibody in the upper panel FIG. 21. The lower panel FIG. 21, showing the signal generated using the phospho-specific antibody, indicates that the peaks resolved in box A are phosphorylated forms, while those resolved in box B are non-phosphorylated at serine 473.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

All patents, patent applications, publications, and references cited herein are expressly incorporated by reference to the same extent as if each individual publication or patent application was specifically and individually indicated to be incorporated by reference.

What is claimed is:

1. A method, comprising:
   resolving in a fluid path one or more analytes in a sample;
   immobilizing in the fluid path at least one of the one or more resolved analytes, the immobilizing being non-specific to any analyte wherein the immobilizing being at least one of photo-immobilizing, chemically immobilizing, or thermally immobilizing; and
   conveying detection agents through the fluid path after the immobilizing, the detection agents configured to bind to or interact with the analytes and facilitate detection of at least one of the immobilized analytes.

2. The method of claim 1, wherein the fluid path comprises a capillary.

3. The method of claim 1, further comprising a plurality of fluid paths, wherein the plurality of fluid paths are capillaries.

4. The method of claim 1, wherein the one or more analytes are resolved by electrophoresis.

5. The method of claim 1, wherein the one or more analytes are resolved by isoelectric focusing, gel electrophoresis, or electrokinetic chromatography.

6. The method of claim 1, wherein the fluid path includes one or more reactive moieties capable of immobilizing the at least one of the one or more analytes in said fluid path, the immobilizing including activating at least one of the one or more reactive moieties.

7. The method of claim 6, wherein the activating comprises photoactivation, chemical activation or thermal activation of the activated reactive moieties.

8. The method of claim 1, wherein the detection agents are conveyed through the fluid path by hydrodynamic flow, electroendosmotic flow, or electrophoresis.

9. The method of claim 1, wherein said detection agents comprise antibodies, peptides, proteins, enzyme substrates, transition state analogs, co factors, nucleotides, polynucleotides, aptamers, lectins, small molecules, ligands, inhibitors, drugs, or labeled molecules thereof, or chemiluminescent substrates.

10. The method of claim 1, wherein said detection agents comprise chemiluminescent labeled antibodies.

11. The method of claim 1, wherein the detection of the at least one of the immobilized analytes includes detecting a chemiluminescent signal.

12. The method of claim 1, wherein the detection of the at least one of the immobilized analytes is by a photodetector.

13. The method of claim 1, wherein the detection of the at least one of the immobilized analytes is by an array of photodetectors.

14. The method of claim 1, wherein the detection of the at least one of the immobilized analytes is by a charged coupled device (CCD) array.

15. The method of claim 1, wherein the resolving and the immobilizing occurs in a same location of the fluid path.

16. The method of claim 1, wherein one or more reactive moieties are disposed within the fluid path prior to the resolving, the one or more reactive moieties configured to immobilize the at least one of the resolved analytes when the one or more reactive moieties are activated.

17. A method, comprising:
   resolving one or more proteins at a location in a capillary;
   photoimmobilizing at least one of the resolved proteins at the location in the capillary;
   contacting the at least one of the photoimmobilized proteins with antibodies to form one or more antibody-protein complexes in the capillary; and
   detecting at least one of the at least one of the photoimmobilized proteins at the location in the capillary after one or more detection agents are conveyed through the capillary.

18. The method of claim 17, wherein said antibodies comprise a label.

19. The method of claim 17, further comprising contacting said one or more antibody-protein complexes with a labeled antibody.

20. The method of claim 17, wherein said detecting includes detecting a chemiluminescent signal.

21. The method of claim 17, wherein the photoimmobilizing is non-specific with respect to any of the one or more resolved proteins.

22. A method, comprising:
   resolving one or more proteins in a location of a capillary, the capillary having one or more photoreactive groups disposed therein;
   photoimmobilizing at least one of the resolved proteins in the location of the capillary;
   introducing antibodies into the capillary such that the antibodies contact the photoimmobilized proteins to form one or more antibody-target complexes in the location of the capillary; and
   detecting in the location of the capillary at least one of the photoimmobilized proteins after one or more detection agents are conveyed through the capillary and contact the one or more antibody-target complexes in the location of the capillary.

23. The method of claim 22, wherein the photoimmobilizing is non-specific with respect to any of the one or more resolved proteins.

24. The method of claim 22, wherein the capillary has disposed therein one or more photoreactive groups and one of polymeric materials or polymerizable materials including one or more photoreactive groups.

25. A method, comprising:
   concentrating one or more proteins in a fluid path;
   immobilizing at least one of the concentrated proteins in the fluid path, the immobilization being non-specific with respect to any of the proteins wherein the immobilizing being at least one of photo-immobilizing, chemically immobilizing, or thermally immobilizing;
   introducing antibodies into the fluid path such that the immobilized proteins contact the antibodies to form one or more antibody-protein complexes in the fluid path; and
   after the introducing, detecting at least one of the immobilized proteins.

26. The method of claim 25, wherein the immobilizing and the detecting occurs in a same location of the fluid path.

27. A method, comprising:

resolving one or more analytes in a location of a fluid path wherein the immobilizing being at least one of photo-immobilizing, chemically immobilizing, or thermally immobilizing;

immobilizing at least one of the resolved analytes in the location of the fluid path;

after the immobilizing, conveying detection agents through the fluid path, the detection agents configured to bind to or interact with the immobilized analytes after the detection agents are conveyed through the fluid path, the detection agents configured to facilitate detection of the immobilized analytes; and detecting at least one of the immobilized analytes.

28. The method of claim 27, wherein the at least one of the resolved analytes are immobilized in the location of the fluid path during the detecting step.

29. The method of claim 27, wherein the detecting occurs in the location of the fluid path.

30. The method of 27, wherein said immobilizing step and said detecting step are carried out by a same device.

31. The method of claim 27, wherein the immobilizing is non-specific with respect to any of the one or more resolved analytes.

* * * * *